(12) United States Patent
Margaron et al.

(10) Patent No.: US 8,106,038 B2
(45) Date of Patent: Jan. 31, 2012

(54) METHOD FOR REDUCING OR PREVENTING PDT RELATED INFLAMMATION

(75) Inventors: Philippe Maria Clotaire Margaron, Burnaby (CA); Anna M. Richter, Vancouver (CA); Julia G. Levy, Vancouver (CA)

(73) Assignee: QLT Inc., Vancouver (CA)

( * ) Notice: Subject to any disclaimer, the term of this patent is extended or adjusted under 35 U.S.C. 154(b) by 0 days.

(21) Appl. No.: 10/081,010

(22) Filed: Feb. 15, 2002

(65) Prior Publication Data

US 2003/0083649 A1 May 1, 2003

Related U.S. Application Data

(60) Provisional application No. 60/269,599, filed on Feb. 15, 2001.

(51) Int. Cl.
*A61K 31/55* (2006.01)
(52) U.S. Cl. .................... 514/185; 514/912
(58) Field of Classification Search ............... 514/185, 514/912
See application file for complete search history.

(56) References Cited

U.S. PATENT DOCUMENTS

| | | | |
|---|---|---|---|
| 4,932,934 A | 6/1990 | Dougherty et al. | 604/21 |
| 5,095,030 A | 3/1992 | Levy et al. | 514/410 |
| 5,171,749 A | 12/1992 | Levy et al. | 514/410 |
| 5,283,255 A | 2/1994 | Levy et al. | 514/410 |
| 5,360,734 A | 11/1994 | Chapman et al. | 435/238 |
| 5,422,362 A | 6/1995 | Vincent et al. | 514/410 |
| 5,707,608 A | 1/1998 | Liu | 424/9.61 |
| 5,756,541 A | 5/1998 | Strong et al. | 514/502 |
| 5,776,966 A | 7/1998 | North | 514/410 |
| 5,789,433 A | 8/1998 | Chan et al. | 514/410 |
| 5,798,349 A | 8/1998 | Levy et al. | 514/185 |
| 5,807,881 A | 9/1998 | Leong et al. | 514/410 |
| 5,834,503 A | 11/1998 | Kelly et al. | 514/410 |
| 5,868,695 A | 2/1999 | Wolf, Jr. et al. | 604/4 |
| 5,882,328 A | 3/1999 | Levy et al. | 604/20 |
| 5,910,510 A | 6/1999 | Strong et al. | 514/502 |
| 5,945,439 A | 8/1999 | Richter et al. | 514/410 |
| 6,008,241 A | 12/1999 | Chan et al. | 514/410 |
| 6,013,053 A | 1/2000 | Bower et al. | 604/96 |
| 6,043,237 A | 3/2000 | Meadows et al. | 514/185 |
| 6,602,274 B1 * | 8/2003 | Chen | 607/88 |

FOREIGN PATENT DOCUMENTS

WO WO 98/34644 8/1998

OTHER PUBLICATIONS

Kennedy et al. "Photodynamic Therapy (PDT) and Photodiagnosis (PD) Using Endogenous Photosensitization Induced by 5-Aminolevulinic Acid (ALA): Mechanisms and Clinical Results" Journal of Clinical Laser Medicine & Surgery 14(5):289-304 (1996).
Marcus et al. "Photodynamic Therapy (PDT) and Photodiagnosis (PD) Using Endogenous Photosensitization Induced by 5-Aminolevulinic Acid (ALA): Current linical and Development Status" Journal of Clinical Laser Medicine & Surgery 14(2):59-66(1996).
Redmond et al. "A Compilation of Singlet Oxygen Yields from Biologically Relevant Molecules" Photochemistry and Photobiology 70(4):391-475 (1999).
Zhou. "Mechanisms of Tumor Necrosis Induced by Photodynamic Therapy" Journal of Photochemistry and Photobiology, B: Biology 3:299-318 (1989).
Simkin, G.O. et al. (1997) *Immunopharmacology* 37:221-230.
US 5,808,054, 09/1998, Brückner et al. (withdrawn)

\* cited by examiner

*Primary Examiner* — Zohreh Fay
(74) *Attorney, Agent, or Firm* — Morrison & Foerster LLP

(57) ABSTRACT

This invention relates generally to the field of pharmacotherapeutics and the use of photodynamic therapy ("PDT"). In particular, the invention provides a method for reducing or preventing the effects of inflammation arising from normal dose photodynamic therapy (PDT), which method comprises exposing a target tissue in a subject that has been treated with normal dose PDT treatment to low dose light having a wavelength absorbed by a photosensitizing agent used in said normal dose PDT treatment for a time sufficient to reduce or prevent the effects of inflammation arising from said normal dose PDT treatment. The method is particularly useful in reducing or preventing the effects of inflammation arising from normal dose PDT treatment of ocular tissues.

31 Claims, 4 Drawing Sheets

FORMULA 1

FORMULA 2

FORMULA 3

FORMULA 4

FORMULA 5

FORMULA 6

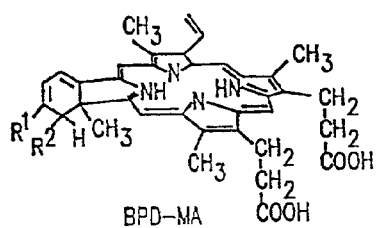
FIGURE 2A
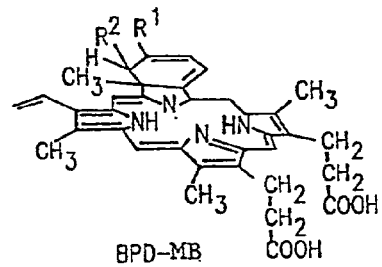
FIGURE 2 B
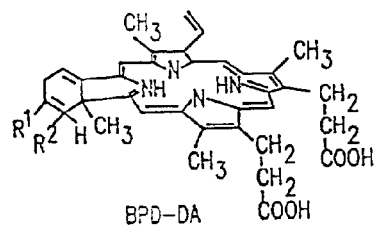
FIGURE 2 C
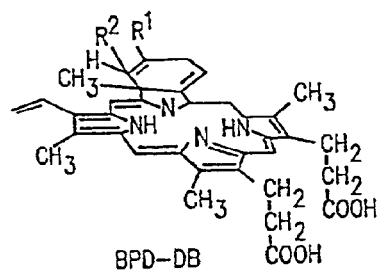
FIGURE 2 D
FIGURE 2

BPD B-ring derivatives verteporfin

METHOD FOR REDUCING OR PREVENTING PDT RELATED INFLAMMATION

RELATED APPLICATIONS

This application claims benefit of priority from U.S. Provisional Patent Application 60/269,599, filed Feb. 15, 2001, which is hereby incorporated by reference in its entirety as if fully set forth.

TECHNICAL FIELD

This invention relates generally to the field of pharmacotherapeutics and the use of photodynamic therapy ("PDT"). In particular, the invention provides a method for reducing or preventing the effects of inflammation arising from normal dose photodynamic therapy (PDT), which method comprises exposing a target tissue in a subject that has been treated with normal dose PDT treatment to low dose light having a wavelength absorbed by a photosensitizing agent used in said normal dose PDT treatment for a time sufficient to reduce or prevent the effects of inflammation arising from said normal dose PDT treatment.

BACKGROUND ART

Photodynamic therapy ("PDT") involves the local or systemic application of a light-absorbing photosensitive agent, usually a porphyrin derivative, which accumulates somewhat selectively in target tissues. Upon irradiation with light of an activating wavelength, reactive oxygen species are produced in cells containing the photosensitizer, which promote cell death. For example, in the treatment of tumors, the photosensitization process is thought to give rise to singlet oxygen, an activated derivative of molecular oxygen, which may oxidatively react with a number of specific sites in cells and tissues. As a consequence, the tumor cells undergo irreversible damage at subcellular levels, especially in the cell membrane and mitochondria. In vivo, tumor destruction is the result of a complex interplay of multiple factors affecting the framework of connective tissue that physically supports the stroma of a tumor and the vascular tissue that nourishes the tumor (Zhou, *J. of Photochem. and Photobiol., B: Biology*, 3:299-318 (1989)).

PDT is known as an approved cancer treatment that can be used for many purposes, such as the treatment of solid tumors (e.g., U.S. Pat. Nos. 4,932,934 and 5,283,255), the impairment of blood-borne targets such as leukemic cells and immunoreactive cells (U.S. Pat. Nos. 5,776,966, 5,807,881, 5,789,433 and 5,868,695), unwanted microorganisms (U.S. Pat. No. 5,360,734), the prevention of restenosis (U.S. Pat. No. 5,422,362), the removal of atherosclerotic plaque (U.S. Pat. No. 5,834,503) and the prevention of transplant rejection (U.S. Pat. No. 5,882,328). PDT has also been used in the diagnosis and treatment of certain neovascular ocular disorders (see e.g., U.S. Pat. Nos. 5,756,541; 5,798,349; and 6,043,237).

U.S. Pat. No. 5,756,541 discloses a method to improve visual acuity in a human subject, which method comprises: irradiating target ocular tissue in said subject with light emitted from a laser, wherein said subject has been administered a formulation of a photoactive compound sufficient to permit an effective amount to localize in said target ocular tissue; wherein the wavelength of the radiation is absorbed by the photoactive compound; and wherein said light radiation is conducted for a time and at an intensity sufficient to improve visual acuity in said subject.

U.S. Pat. No. 5,798,349 discloses a method to treat conditions of the eye characterized by unwanted neovasculature, which method comprises: administering to a primate subject in need of such treatment an amount of liposomal formulation of green porphyrin sufficient to permit an effective amount to localize in said neovasculature; permitting sufficient time to elapse to allow an effective amount of said green porphyrin to localize in said neovasculature; and irradiating the neovasculature with light from a laser, said light being absorbed by the green porphyrin so as to occlude said neovasculature.

U.S. Pat. No. 6,043,237 discloses a method to prevent or inhibit the development of secondary cataract in the eye of a subject following removal of the lens during cataract surgery, which method comprises: administering to the lens capsule of a subject an amount of a green porphyrin sufficient to permit an effective amount to localize in lens epithelial cells that remain following said surgery; permitting a sufficient time to elapse to allow said effective amount of green porphyrin to localize in said lens epithelial cells; and irradiating said lens epithelial cells with light that is absorbed by the green porphyrin at an energy level sufficient to destroy substantially all of said lens epithelial cells.

Although PDT can be used in the treatment of many diseases or disorders including ocular disease or disorders, its use is sometimes limited because normal therapeutic dose of PDT causes inflammation. For example, the fact that normal dose PDT can cause a localized inflammatory response is discussed in WO 98/34644. It is believed that the inflammation can ultimately result in angiogenesis. When normal dose PDT is used to treat ocular neovascularization, e.g., with verteporfin, although the immediate result is destruction of unwanted neovascular tissue, subsequent PDT-induced inflammation could potentially promote neovascularization in and around the treated area, thereby partially abrogating the benefit of treatment. Therefore, there exists in the art a need for methods that can reduce or prevent the effects of inflammation arising from normal dose PDT treatment. The present invention addresses this and other related needs in the art.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

DISCLOSURE OF THE INVENTION

This invention relates generally to the field of pharmacotherapeutics and the use of photodynamic therapy ("PDT"). In one aspect, the invention is directed to a method for reducing or preventing the effects of inflammation arising from normal dose photodynamic therapy (PDT), which method comprises exposing a target tissue in a subject that has been treated with normal dose PDT treatment to low dose light having a wavelength absorbed by a photosensitizing agent used in said normal dose PDT treatment for a time sufficient to reduce or prevent the effects of inflammation arising from said normal dose PDT treatment.

The present method can be used to reduce or prevent inflammation caused by normal dose PDT treatment of any target tissue. Preferably, the target tissue is an ocular tissue. More preferably, the target ocular tissue contains unwanted neovasculature, e.g., choroidal neovasculature. The target tissue may also be a tumor or cancer tissue, e.g., tumors or cancers of the connective, epithelium, muscle or nerve tissue origin.

The present method can also be used to reduce or prevent inflammation caused by normal dose PDT treatment of a subject, e.g., a human, diagnosed or afflicted with various ocular diseases or disorders. Exemplary ocular diseases or disorders include macular degeneration, e.g., age-related macular degeneration (AMD), ocular histoplasmosis syndrome, pathologic myopia, neovascular glaucoma, diabetic retinopalthy, diabetic macular edema, corneal neovascularization, choroidal neovascularization or other ocular inflammatory diseases.

Any photosensitizing agents, including tetrapyrrolic, polypyrrolic or related macrocycles, including texaphyrins, chlorins, phthalocyanines, purpurins, bacteriochlorins, porphyrins and any other porphyrin derivatives such as PHOTOFRIN® porfimer sodium, green porphyrins, phthalocyanines and 5-aminolevulinic acid (ALA), that are suitable for PDT can be used in the present methods. Preferably, the photosensitizing agent being used comprises one or more monohydrobenzoporphyrin compounds. Also preferably, the photosensitizing agent being used comprises BPD-MA or verteporfin. More preferably, certain BPD B-ring derivatives, whether hydrophilic or lipophilic, can be used in the present method. Tin ethyl etiopupurin and motexafin luthetium can also be used.

The photosensitizing agent can be applied to the target tissue by any suitable method known in the art. For example, the photosensitizing agent can be applied topically to the target tissue. Alternatively, the photosensitizing agent can be administered systemically.

To effectively reduce or prevent inflammation caused by normal dose PDT treatment of a target tissue, the target tissue should be subjected to low dose light radiation soon before or after the target tissue is treated with the normal dose PDT. The target tissue may be subjected to low dose radiation immediately after the target tissue has been treated with the normal dose PDT. Preferably, the time gap between the low dose and the normal dose radiation is from immediately after to several hours after normal dose light radiation, preferably from immediately to about 15 minutes after normal dose light radiation.

The dosage and exposing time of the low dose PDT treatment can be decided, e.g., empirically, in view of the subject treated with the normal dose PDT treatment, the location of the target tissue in the subject, the dosage of the photosensitizing agent delivered to the target tissue, and the dosage and exposing time of the preceding normal dose PDT treatment. Because the total PDT dose depends on a combination of the dose of the photosensitizing agent and the dose of the irradiating light, low-dose PDT may be administered in combinations of relatively high photosensitizer doses and low light doses or, on the other hand, combinations of relatively low photosensitizer doses and high light doses. The latter low photosensitizer/high light combination can also be achieved by administering a relatively normal dose of photosensitizer, followed by an unusually long "clearance" time before being irradiated with light. Therefore, a wide variety of conditions, all producing a relatively low dose of PDT overall, would be suitable for the invention.

The low dose light can be achieved, in view of the area to be treated, the manner and dose of photosensitizing agent administered and the time gap between the normal and low dose irradiation, by an appropriate combination of the wavelength of the light, the intensity of the light source, the total light dosage and exposing time. Generally, low dose PDT should be carried out under conditions that are sub-cytotoxic for the target tissues. In a specific embodiment, where low dose PDT is carried out immediately after normal dose PDT, the light dose required is generally in the range from about $\frac{1}{20}$ to about $\frac{1}{2}$ of the light used for the normal dose. Low dose PDT should be viewed as PDT to deliver a reduced energy dose (in $J/cm^2$) relative to the energy dose (in $J/cm^2$) of a previous "normal" PDT treatment.

For irradiation with low dose light, the intensity (or fluence rate) of the light source should not exceed 600 $mW/cm^2$, the intensity (or total dose) of the irradiation should not exceed 100 $J/cm^2$, and the exposing time should not exceed 2 minutes. Preferably, the dosage of the low dose light is about 15 $J/cm^2$. The low dose irradiation lasts from about 10 seconds to about 15 minutes. Preferably, the low dose irradiation lasts about 25 seconds.

In general, the area exposed to low dose PDT should overlap with and may be somewhat larger than the area exposed to radiation under normal dose PDT. Preferably, the entire area exposed to the normal dose PDT is included in the low dose treatment. Also preferably, the area exposed to the low dose light in the target tissue should be concentric with but larger than the area exposed to the normal dose PDT treatment. The area exposed to the low dose light is at least about 1 or 1.5-10 times, preferably, about 1-3 times of the area exposed to the normal dose PDT treatment.

The wavelength of the light source should be within a range absorbed by the photosensitizing agents used in the normal dose irradiation. Preferably, the wavelength of the light source is from about 350 nm to about 800 nm. More preferably, the wavelength of the light source is from about 400 nm to about 750 nm, e.g., at 689 nm.

Inflammation can be monitored by any methods known in the art including photography or immunohistochemistry. In a specific embodiment, the inflammation is monitored by photography such as fluorescein angiography or fundus photography. The inflammation markers that can be monitored by fluorescein angiography or fundus photography include, but are not limited to, retinal whitening, localized retinal elevation, depigmented treatment area with hyperpigmentation, early hypofluorescence in the treatment area, hyperfluorescence at the border, late pooling, central hypofluorescence and blocked fluorescence and window defects. In another specific embodiment, the inflammation is monitored by immunohistochemistry when the subject to be treated is an animal. The inflammation markers that can be monitored by immunohistochemistry include, but are not limited to, CD4, CD8, CD31, macrophage and MHC II. Preferably, methods for monitoring inflammation clinically, such as "scanning laser opthalmoscopy (SLO)" and "optical coherence tomography (OCT)" are used, especially in treating humans.

The method may further comprise a step of administering an immunosuppressive agent, a neuroprotective agent, and/or an antiangiogenic agent to the target tissue before the target tissue is exposed to the normal or low dose light. The immunosuppressive agent, the neuroprotective agent, and/or the antiangiogenic agent can be administered before or after PDT treatment. Preferably, the immunosuppressive agent, the neuroprotective agent, and/or the antiangiogenic agent is administered before the PDT treatment, e.g., being administered to the target tissue with the photosensitizing agent simultaneously.

In another aspect, the invention is directed to a method of treating unwanted neovasculature of an eye, which method comprises: a) administering to a subject in need of such treatment an amount of photosensitizer sufficient to permit an effective amount to localize in said neovasculature; b) permitting sufficient time to elapse to allow an effective amount of said photosensitizer to localize in said neovasculature; c) providing a first dosage of irradiation to a treatment area of the subject's eye containing said neovasculature with light having a wavelength that is absorbed by said photosensitizer for a sufficient time and at a sufficient intensity to occlude said neovasculature; and d) providing a second dosage of irradiation to said treatment area and/or said treatment area plus an additional area encompassing said treatment area with light having a wavelength absorbed by the photosensitizer for sufficient time to reduce or prevent the effects of inflammation arising from irradiation of said treatment area, wherein the second dosage of irradiation is lower than the first dosage of irradiation.

Any unwanted neovasculature of the eye can be treated with the present method. Preferably, the unwanted neovasculature to be treated is in the choroid of the subject's eye, and wherein the subject has been diagnosed or is afflicted with AMD, pathologic myopia, or ocular histoplasmosis.

The invention also includes use of a photosensitizer in the preparation of a medicament for use in any of the methods described herein.

BRIEF DESCRIPTION OF THE DRAWINGS

FIG. 2 shows the structure of four BPD-type compounds useful as photosensitizing agents in the methods of the invention.

MODES OF CARRYING OUT THE INVENTION

A. Definitions

Figure 1:
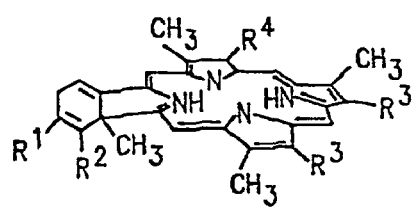
FIG. 1 shows the formulas of typical green porphyrins useful in the methods of the invention.
Figure 1:
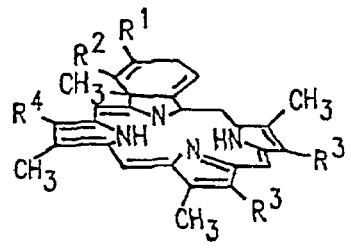
Figure 1:
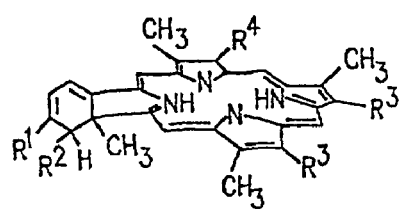
Figure 1:
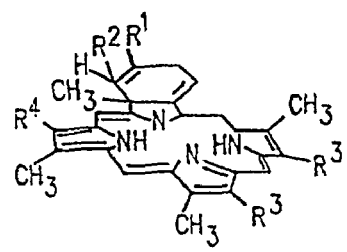
Figure 1:
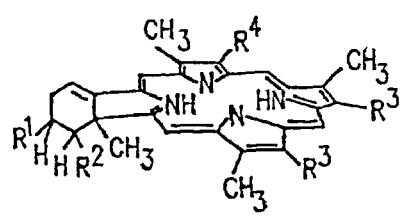
Figure 1:
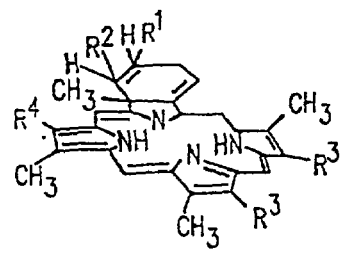

Unless defined otherwise, all technical and scientific terms used herein have the same meaning as is commonly understood by one of ordinary skill in the art to which this invention belongs. All patents, applications, published applications and other publications and other data bases referred to herein are incorporated by reference in their entireties.

As used herein, "a" or "an" means "at least one" or "one or more."

As used herein, a "photosensitizing agent," "photoactive compound" or "photosensitizer" refers to a chemical compound that, when exposed to light of a wavelength capable of being absorbed by the photosensitizer, absorbs light energy to result in the desired physiological effect. The photosensitizing agents that can be used in the present methods preferably have an absorption spectrum that is within the range of wavelengths between 350 nm and 1200 nm, which absorption spectrum may be tailored to the desired penetration in a manner known per se, preferably between about 400 and 900 nm and, most preferably, between 600 and 800 nm. Another property of photosensitizers in general that is of particular significance in the practice of the present invention is a relative absence of toxicity to cells in the absence of the photochemical effect and the ready clearance from tissues in the absence of a target-specific interaction between particular cells and the photosensitizer.

As used herein, "inflammation" refers to the series of changes that occur in a living body following an injury. The injury may be caused by physical agents, such as excessive heat or cold, pressure, ultraviolet or ionizing irradiation, cuts or abrasions; by a wide variety of inorganic or organic chemical substances; or by biological agents such as viruses, bacteria, and other parasites; or by disease processes such as diabetic macular edema, autoimmune disease or macular degeneration; or as a side effect of normal dose PDT treatment. The present invention provides a skilled artisan with the ability to use low dose PDT to treat or prevent undesirable inflammation resulting from a previous normal dose PDT treatment.

As used herein, "normal dose light" refers to a dosage of light, at a wavelength capable of being absorbed by the photosensitizer, that is sufficient to achieve the preventive or therapeutic purpose of the PDT treatment and causes inflammation in the target tissue.

As used herein, "low dose light" refers to a dosage of light, at a wavelength capable of being absorbed by the photosensitizer, that does not cause evident cell damage, necrosis or erythema, but is sufficient to prevent or reduce the inflammation caused by the preceding normal dose PDT treatment. For example, a low dose light radiation should be sufficient to reduce the inflammation caused by the preceding normal dose PDT treatment by at least 50%. Preferably, a low dose light radiation is sufficient to reduce the inflammation caused by the preceding normal dose PDT treatment by at least about 60%, about 70%, about 80%, about 90%, about 95%, about 99%, and most preferably, completely prevent the inflammation. The low dose light radiation can be achieved, in view of the area to be treated, the manner and dose of photosensitizing agent administered and the time gap between the normal and low dose irradiation, by an appropriate combination of the wavelength of the light, the intensity of the light source, the total light dosage and exposing time. For irradiation with low dose light, the intensity of the light source should not exceed 600 mW/cm$^2$, the intensity of the irradiation should not exceed 100 J/cm$^2$, and the exposing time should not exceed 2 minutes.

As used herein, "tissue" refers to a collection of similar cells and the extracellular substances surrounding them. There are four basic tissues in the body: 1) epithelium; 2) connective tissues, including blood, bone, and cartilage; 3) muscle tissue; and 4) nerve tissue.

As used herein, "immunosuppressive agent" refers to substances that act to suppress or mask leukocyte responses. This would include substances that suppress cytokine production, down-regulate or suppress self-antigen expression, or mask the MHC antigens.

As used herein, "light," "radiation," "irradiation," and variations of these terms refer to any of a variety of wavelengths of electromagnetic radiation including or excluding wavelengths of the visible light spectra. For example, and unless other wise indicated, these terms are meant generally to refer to the visible light range of the electromagnetic spectrum, generally including wavelengths between about 350 nm and about 800 nm. In addition, these terms may also be used herein to refer to electromagnetic radiation within the ultraviolet (including wavelengths below about 400 nm) and infrared spectra (including wavelengths above about 700 nm).

As used herein, "target tissue" refers to tissues and/or regions of a subject selected for PDT treatment. Further, this term refers to the region exposed to irradiation during treatment with PDT. This term is not meant to be limiting in terms of the area exposed to low dose light or irradiation in the present invention. As indicated herein, the area exposed to low dose light contains all or part of the area previously treated with higher dose PDT. The area exposed to low dose light may be concentric with, as well as equal to or larger than, the area previously treated.

B. Photosensitizing Agents

For clarity of disclosure, and not by way of limitation, the detailed description of the invention is divided into the subsections that follow.

The photosensitizer or photosensitizing agent used in the normal dose and/or low dose PDT can be any photosensitizing agent suitable for photodynamic therapy ("PDT") that is capable of penetrating into the target cells to be treated and causing the desired degree of biodistribution in a desired period of time. Whether this criterion is met by a potential photosensitizer candidate can be easily and quickly determined, for example, by the following simple test:

1. Prepare live cultured cells (preferably from a suspension grown culture; any cell line is suitable).
2. Add the photosensitizer being tested to the cells at concentrations of 1-3 ug/mL, in the presence of 10% serum.
3. Remove the excess photosensitizer drug by centrifugation following various periods of incubation (e.g., 5, 15, 30 and 60 minutes).
4. Wash the cells with phosphate-buffered saline and lyse them by freeze-thawing.
5. Determine the concentration of a tested photosensitizer in cell lysates by fluorescence against appropriate standards.

Figure 4:
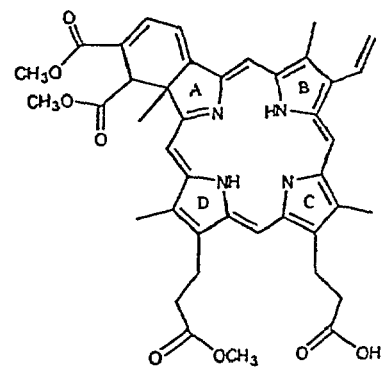
FIG. 4 shows the structure of verteporfin useful as photosensitizing agents in the methods of the invention.

Any photosensitizing agents, including porphyrins such as PHOTOFRIN® porfimer sodium, porphyrin derivatives, green porphyrins, phthalocyanines and 5-aminolevulinic acid (ALA), that are suitable for PDT can be used in the present methods (U.S. Pat. No. 5,910,510; Kennedy et al., *J. Clin. Laser Med. Surg.*, 14(5):289-304 (1996); and Marcus et al., *J. Clin. Laser Med. Surg.*, 14(2):59-66 (1996)). Preferably, the photosensitizing agent being used comprises one or more monohydrobenzoporphyrin compounds. Also preferably, the photosensitizing agent being used comprises BPD-MA or verteporfin (FIG. 4), e.g., VISUDYNE™ (CIBA Vision, A Novartis Company). VISUDYNE™ (verteporfin for injection) is a light activated drug used in photodynamic therapy. The finished drug product is a lyophilized dark green cake. Verteporfin is a 1:1 mixture of two regioisomers (I and II). The chemical names for the verteporfin regioisomers are: 9-methyl (I) and 13-methyl (II) trans-(±)-18-ethenyl-4,4a-dihydro-3,4-bis(methoxycarbonyl)-4a,8,14,19-tetramethyl-23H,25H-benzo[b]porphine-9,13-dipropanoate. In addition, photosensitizing agents disclosed or used in the following U.S. Pat. Nos. can be used in the methods of the present invention: U.S. Pat. Nos. 6,013,053; 6,008,241; 5,945,439; 5,910,510; 5,808,054; 5,882,328; 5,834,503; 5,756,541; and 5,707,608.

A particularly potent group of photosensitizers includes green porphyrins, which are described in detail in Levy et al., U.S. Pat. No. 5,171,749 issued Dec. 15, 1992, which is incorporated herein by reference. The term "green porphyrins" refers to porphyrin derivatives obtained by reacting a porphyrin nucleus with an alkyne in a Diels-Alder type reaction to obtain a mono-hydrobenzoporphyrin. Typically, green porphyrins are selected from a group of porphyrin derivatives obtained by Diels-Alder reactions of acetylene derivatives with protoporphyrin under conditions that promote reaction at only one of the two available conjugated, nonaromatic diene structures present in the protoporphyrin-IX ring systems (rings A and B).

Several structures of typical green porphyrins are shown in FIG. 1. The Diels-Alder reaction initially results in the formation of a cyclohexadiene—referred to herein as "hydrobenzo"—fused to the A or B pyrrolic ring, as shown in formulas 1 and 2 of FIG. 1. Rearrangement of the π system in the hexadiene ring results in the formation of compounds of formulas 3 and 4, and reduction would provide compounds of formulas 5 and 6. For practical reasons, however, the compounds of formulas 5 and 6 are preferably made by performing the previously discussed Diels-Alder reaction with the corresponding olefin being substituted for the usual acetylene compound, thus producing a more reduced version of the resulting porphyrin ring structure. These compounds are shown in formulas 1-6 with hydrogen occupying the internal ring nitrogens. However, it is to be understood that the metalated forms, in which a cation replaces one or both of these hydrogens, can also be used. The preparation of the green porphyrin compounds useful in this invention is described in detail in U.S. Pat. No. 5,095,030.

For convenience, an abbreviation of the term hydromonobenzoporphyrin derivative—"BPD"—is generally used to refer to compounds of formulas 3 and 4 of FIG. 1. Compounds of the formulas 3 and 4 and mixtures thereof are particularly preferred. The compounds of formulas BPD-MA and BPD-MB may be homogeneous, in which only the C ring carbalkoxyethyl or only the D ring carbalkoxyethyl would be hydrolyzed, or may be mixtures of the C and D ring substituent hydrolyzates. In addition, mixtures of any two or more of BPD-MA, -MB, -DA and -DB can be used in the methods of and compositions of the invention (FIG. 2).

Figure 3:
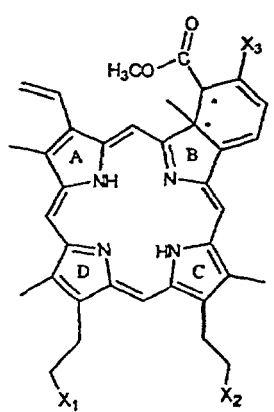
FIG. 3 shows the formulas of BPD B-ring derivatives useful as photosensitizing agents in the methods of the invention.
Figure 5:
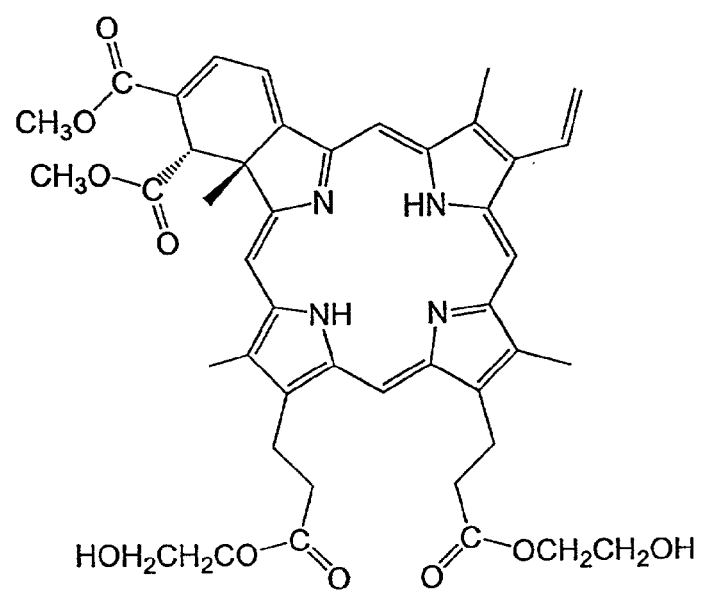
FIG. 5 shows the structure of QLT0074 (A-EA6) useful as photosensitizing agents in the methods of the invention.

A number of BPD B-ring derivatives may also be used in the present methods (see FIG. 3 and the following Tables 1 and 2). QLT0074 (A-EA6) as disclosed in FIG. 5 can also be used in the methods of the present invention.

TABLE 1

Hydrophilic BPD B-ring analogs

| Drug | X1 | X2 | X3 |
|---|---|---|---|
| QLT0061 | COOH | COOH | COOH |
| QLT0077 | $CONH(CH_2)_2N^+(CH_3)_3I^-$ | $CONH(CH_2)_2N^+(CH_3)_3I^-$ | $COOCH_3$ |
| QLT0079 | $CONH(CH_2)_2N^+(CH_3)_2((CH_2)_3CH_3$ | $CONH(CH_2)_2N^+(CH_3)_2((CH_2)_3CH_3)$ | $COOCH_3$ |
| QLT0086[1] | $CONHCH(COOH)CH_2COOH$ | $CONHCH(COOH)CH_2COOH$ | $COOCH_3$ |
| QLT0092[2] | $CONH(CH_2)_2NH(CH_3)_2$ $CF_2COO^-$ | $CONH(CH_2)_2NH(CH_3)_2$ $CF_3COO-$ | $COOCH_3$ |
| QLT0094 | $CONHCH_2COOH$ | $CONHCH_2COOH$ | $CONHCH_2COOH$ |

[1]Batch contains trace amounts of $CF_3COO^-$.
[2]Batch contains 4 × ($CF_3COO^-$).

TABLE 2

Lipophilic BPD B-ring analogs

| Drug | X1 | X2 | X3 |
|------|----|----|----|
| QLT0060 | $CO(O(CH_2)_2)OH$ | $CO(O(CH_2)_2)OH$ | $COOCH_3$ |
| QLT0069 | $COOCH_3$ | $COOCH_3$ | $COOH$ |
| QLT0078 | $CO(O(CH_2)_2)_2OH$ | $CO(O(CH_2)_2)_2OH$ | $COOCH_3$ |
| QLT0080 | $CO(O(CH_2)_2)_3OH$ | $CO(O(CH_2)_2)_3OH$ | $COOCH_3$ |
| QLT0081 | $CO(O(CH_2)_2)_2OCH_3$ | $CO(O(CH_2)_2)_2OCH_3$ | $CO(O(CH_2)_2)_2OCH_3$ |
| QLT0082 | $CO(O(CH_2)_2)_2OH$ | $CO(O(CH_2)_2)_2OH$ | $CO(O(CH_2)_2)_2OH$ |
| QLT0083 | $CO(O(CH_2)_2)_3OH$ | $CO(O(CH_2)_2)_3OH$ | $CO(O(CH_2)_2)_3OH$ |
| QLT0087 | $CO(O(CH_2)_2)_4OH$ | $CO(O(CH_2)_2)_4OH$ | $COOCH_3$ |
| QLT0088 | $COOCH_3$ | $COOCH_3$ | $CONH(C_6H_4)(C_5H_{10}N)$ |
| QLT0090 | $CO(O(CH_2)_2)_5OH$ | $CO(O(CH_2)_2)_5OH$ | $COOCH_3$ |
| QLT0093 | $CO(O(CH_2)_2)_5OH$ | $CO(O(CH_2)_2)_5OH$ | $CO(O(CH_2)_2)_5OH$ |

Other photosensitizing agents that can be used in the present methods include angelicins, some biological macromolecules such as lipofuscin; photosystem II reaction centers; and D1-D2-cyt b-559 photosystem II reaction centers, chalcogenapyrillium dyes, chlorins, chlorophylls, coumarins, cyanines, certain DNA and related compounds such as adenosine; cytosine; 2'-deoxyguanosine-5'-monophosphate; deoxyribonucleic acid; guanine; 4-thiouridine; 2'-thymidine-5'-monophosphate; thymidylyl(3'-5')-2'-deoxyadenosine; thymidylyl(3'-5')-2'-deoxyguanosine; thymine; and uracil, certain drugs such as adriamycin; afloqualone; amodiaquine dihydrochloride; chloroquine diphosphate; chlorpromazine hydrochloride; daunomycin; daunomycinone; 5-iminodaunomycin; doxycycline; furosemide; gilvocarcin M; gilvocarcin V; hydroxychloroquine sulfate; lumidoxycycline; mefloquine hydrochloride; mequitazine; merbromin (mercurochrome); primaquine diphosphate; quinacrine dihydrochloride; quinine sulfate; and tetracycline hydrochloride, certain flavins and related compounds such as alloxazine; flavin mononucleotide; 3-hydroxyflavone; limichrome; limiflavin; 6-methylalloxazine; 7-methylalloxazine; 8-methylalloxazine; 9-methylalloxazine; 1-methyl limichrome; methyl-2-methoxybenzoate; 5-nitrosalicyclic acid; proflavine; and riboflavin, flullerenes, metalloporphyrins, metallophthalocyanines, methylene blue derivatives, naphthalimides, naphthalocyanines, certain natural compounds such as bis(4-hydroxy-3-methoxyphenyl)-1,6-heptadiene-3,5-dione; 4-(4-hydroxy-3-methoxyphenyl)-3-buten-2-one; N-formylkynurenine; kynurenic acid; kynurenine; 3-hydroxykynurenine; DL-3-hydroxykynurenine; sanguinarine; berberine; carnane; and 5,7,9(11),22-ergostatetraene-3β-ol, nile blue derivatives, NSAIDs (nonsteroida anti-inflammatory drugs), perylenequinones, phenols, pheophorbides, pheophytins, photosensitizer dimers and conjugates, phthalocyanines, porphycenes, porphyrins, psoralens, purpurins, quinones, retinoids, rhodamines, thiophenes, verdins, vitamins and xanthene dyes (Redmond and Gamlin, *Photochem. Photobiol.*, 70(4):391-475 (1999)).

Exemplary angelicins include 3-aceto-angelicin; angelicin; 3,4'-dimethyl angelicin; 4,4'-dimethyl angelicin; 4,5'-dimethyl angelicin; 6,4'-dimethyl angelicin; 6,4-dimethyl angelicin; 4,4',5'-trimethyl angelicin; 4,4',5'-trimethyl-1'-thioangelicin; 4,6,4'-trimethyl-1'-thioangelicin; 4,6,4'-trimethyl angelicin; 4,6,5'-trimethyl-1'-thioangelicin; 6,4,4'-trimethyl angelicin; 6,4',5'-trimethyl angelicin; 4,6,4',5'-tetramethyl-1'-thioangelicin; and 4,6,4',5'-tetramethyl angelicin.

Exemplary chalcogenapyrillium dyes include pyrilium perchlorate, 4,4'-(1,3-propenyl)-bis[2,6-di(1,1-dimethyl-ethyl)]-; pyrilium perchlorate, 2,6-bis (1,1-dimethyl-ethyl)-4-[1-[2,6-bis(1,1-dimethyl-ethyl)selenopyran-4-ylidene]-3-propenyl-; pyrilium hexofluoro phosphate, 2,6-bis-(1,1-dimethyl-ethyl)-selenopyran-4-ylidene]-3-propenyl-; pyrilium hexofluoro phosphate, 2,6-bis(1,1-dimethyl-ethyl)-selenopyran-4-ylidene]-3-propenyl-; pyrilium perchlorate, 2,6-bis(1,1-dimethyl-ethyl)-4-[1-[2,6-bis(1,1-dimethyl-ethyl) telluropyran-4-ylidene]-3-propenyl-; pyrilium hexofluoro phosphate, 2,6-bis (1,1-dimethyl-ethyl)-4-[1-[2,6-bis (1,1-dimethyl-ethyl)telluropyran-4-ylidene]-3-propenyl-; pyrilium perchlorate, 2,6-bis(1,1-dimethyl-ethyl)-4-[1-[2,6-bis(1,1-dimethyl-ethyl) thiapyran-4-ylidene]-3-propenyl]-; selenopyrilium hexofluoro phosphate, 2,6-bis (1,1-dimethyl-ethyl)-4-[1-[2,6-bis(1,1-dimethyl-ethyl)selenopyran-4-ylidene]-3-propenyl]-; selenopyrilium, 2,6-bis(1,1-dimethyl-ethyl)-4-[1-[2,6-bis(1,1-dimethylethyl) selenopyran-4-ylidene]-3-propenyl-; selenopyrilium percheorate, 2,6-bis (1,1-dimethyl-ethyl)-4-[1-[2,6-bis(1,1-dimethyl-ethyl)-4-[1-[2,6-bis (1,1-dimethyl-ethyl)telluropyran-4-ylidene]-3-propenyl]-; selenopyrilium hexofluoro phosphate, 2,6-bis (1,1-dimethyl-ethyl)-4-[1-[2,6-bis(1,1-dimethyl-ethyl) telluropyran-4-ylidene]-3-propenyl]-; selenopyrilium hexofluoro phosphate, 2,6-bis(1,1-dimethyl-ethyl)-4-[2-[2,6-bis (1,1-dimethyl-ethyl)selenopyran-4-ylidene]-4-(2-butenyl)]-; selenopyrilium hexofluoro phosphate, 2,6-bis(1,1-dimethyl-ethyl)-4-[2-[2,6-bis(1,1-dimethyl-ethyl) selenopyran-4-ylidene]-4-(2-pentenyl)]-; telluropyrilium tetrafluoroborate, 2,6-bis (1,1-dimethyl-ethyl)-4-[1-[2,6-bis(1,1-dimethyl-ethyl)-telluropyran-4-ylidene]-3-propenyl]-; telluropyrilium hexofluoro phosphate, 2,6-bis(1,1-dimethyl-ethyl)-4-[1-[2,6-bis (1,1-dimethyl-ethyl)telluropyran-4-ylidene]-3-propenyl]-; telluropyrilium hexofluoro phosphate, 2,6-bis(1,1-dimethyl-ethyl)-4-[1-[2,6-bis(1,1-dimethyl-ethyl)telluropyran-4-ylidene]ethyl-; telluropyrilium hexofluoro phosphate, 2,6-bis(1,1-dimethyl-ethyl)-4-[1-[2,6-bis (1,1-dimethyl-ethyl)-telluropyran-4-ylidene] methyl-; thiopyrilium hexofluoro phosphate, 2,6-bis(1,1-dimethyl-ethyl)-4-[1-[2,6-bis(1,1-dimethyl-ethyl) thiopyran-4-ylidene]-3-propenyl]-; thiopyrilium hexofluoro phosphate, 2,6-bis (1,1-dimethyl-ethyl)-4-[1-[2,6-bis(1,1-dimethyl-ethyl)selenopyran-4-ylidene]-3-propenyl]-; and thiopyrilium hexofluoro phosphate, 2,6-bis(1,1-dimethyl-ethyl)-4-[1-[2,6-bis (1,1-dimethyl-ethyl)telluropyran-4-ylidene]-3-propenyl]-.

Exemplary chlorins dyes include 5-azachlorin dimethyl ester derivative; 5,10,15,20-tetrakis-(m-hydroxyphenyl) bacteriochlorin; benzoporphyrin derivative monoacid ring A; benzoporphyrin derivative monoacid ring-A; porphine-2,18-dipropanoic acid, 7-[2-dimethyl-amino)-2-oxoethyl]-8-ethylidene-7,8-dihydro-3,7,12,17-tetramethyl, dimethylester; porphine-2,18-dipropanoic acid, 7-[2-dimethyl-amino)-2- oxoethyl]-8-ethylidene-7,8-dihydro-3,7,12,17-tetramethyl, dimethylester Z; porphine-2,18-dipropanoic acid, 7-[2-dimethyl-amino)-2-oxoethyl]-8-ethylidene-8-ethyl-7,8-dihydro-3,7,12,17-tetramethyl, dimethylester Z ECHL; porphine-2, 18-dipropanoic acid, 7-[2-dimethyl-amino)-2-oxoethyl]-8-ethylidene-8-n-heptyl-7,8-dihydro-3,7,12,17-tetramethyl, dimethylester Z; tin (II) porphine-2,18-dipropanoic acid, 7-[2-(dimethylamino-2-oxoethyl]-8-ethylidene-8-n-heptyl-7,8-dihydro-3,7,12,17-tetramethyl, dimethylester Z; chlorin $e_6$; chlorin $e_6$ dimethyl ester; chlorin $e_6k_3$; chlorin $e_6$ monomethyl ester; chlorin $e_6$ $Na_3$; chlorin $p_6$; chlorin $p_6$-trimethylester; chlorin derivative zinc (II) porphine-2,18-dipropanoic acid, 7-[2-(dimethylamino)-2-oxoethyl]-8-ethylidene-8-n-heptyl-7,8-dihydro-3,7,12,17-tetramethyl, dimethylester Z; $13^1$-deoxy-20-formyl-vic-dihydroxy-bacteriochlorin di-tert-butyl aspartate; $13^1$-deoxy-20-formyl-4-keto-bacteriochlorin di-tert-butyl aspartate; di-L-aspartyl chlorin $e_6$; mesochlorin; 5,10,15,20-tetrakis-(m-hydroxyphenyl)chlorin; meta-(tetrahydroxyphenyl)chlorin; methyl-$13^1$-deoxy-20-formyl-4-keto-bacteriochlorin; mono-L-aspartyl chlorin $e_6$; photoprotoporphyrin IX dimethyl ester; phycocyanobilin dimethyl ester; protochlorophyllide a; tin (IV) chlorin $e_6$; tin chlorin $e_6$; tin L-aspartyl chlorin $e_6$; tin octaethyl-benzochlorin; tin (IV) chlorin; zinc chlorin $e_6$; and zinc L-aspartyl chlorin $e_6$.

Exemplary chlorophylls dyes include chlorophyll a; chlorophyll b; oil soluble chlorophyll; bacteriochlorophyll a; bacteriochlorophyll b; bacteriochlorophyll c; bacteriochlorophyll d; protochlorophyll; protochlorophyll a; amphiphilic chlorophyll derivative 1; and amphiphilic chlorophyll derivative 2.

Exemplary coumarins include 3-benzoyl-7-methoxycoumarin; 7-diethylamino-3-thenoylcoumarin; 5,7-dimethoxy-3-(1-naphthoyl) coumarin; 6-methylcoumarin; 2H-selenolo [3,2-g] [1]benzopyran-2-one; 2H-selenolo[3,2-g] [1]benzothiopyran-2-one; 7H-selenolo[3,2-g] [1]benzoseleno-pyran-7-one; 7H-selenopyrano[3,2-f] [1]benzofuran-7-one; 7H-selenopyrano[3,2-f] [1]benzo-thiophene-7-one; 2H-thienol[3,2-g] [1][1]benzopyran-2-one; 7H-thienol[3,2-g] [1]benzothiopyran-7-one; 7H-thiopyrano[3,2-f] [1]benzofuran-7-one; coal tar mixture; khellin; RG 708; RG277; and visnagin.

Exemplary cyanines include benzoselenazole dye; benzoxazole dye; 1,1'-diethyloxacarbocyanine; 1,1'-diethyloxadicarbocyanine; 1,1'-diethylthiacarbocyanine; 3,3'-dialkylthiacarbocyanines (n=2-18); 3,3'-diethylthiacarbocyanine iodide; 3,3'-dihexylselenacarboccyanine; kryptocyanine; MC540 benzoxazole derivative iodide; MC540 quinoline derivative; merocyanine 540; and meso-ethyl, 3,3'-dihexylselenacarbocyanine.

Exemplary fullerenes include $C_{60}$; $C_{70}$; $C_{76}$; dihydrofullerene; 1,9-(4-hydroxy-cyclohexano)-buckminsterfullerene; [1-methyl-succinate-4-methyl-cyclohexadiene-2, 3]-buckminster-fullerene; and tetrahydro fullerene.

Exemplary metalloporphyrins include cadmium (II) chlorotexaphyrin nitrate; cadmium (II) meso-diphenyl tetrabenzoporphyrin; cadmium meso-tetra-(4-N-methylpyridyl)-porphine; cadmium (II) texaphyrin; cadmium (II) texaphyrin nitrate; cobalt meso-tetra-(4-N-methylpyridyl)-porphine; cobalt (II) meso(4-sulfonatophenyl)-porphine; copper hematoporphyrin; copper meso-tetra-(4-N-methylpyridyl)-porphine; copper (II) meso(4-sulfonatophenyl)-porphine; Europium (III) dimethyltexaphyrin dihydroxide; gallium tetraphenylporphyrin; iron meso-tetra(4-N-methylpyridyl)-porphine; lutetium (III) tetra(N-methyl-3-pyridyl)-porphyrin chloride; magnesium (II) meso-diphenyl tetrabenzoporphyrin; magnesium tetrabenzoporphyrin; magnesium tetraphenylporphyrin; magnesium (II) meso(4-sulfonatophenyl)-porphine; magnesium (II) texaphyrin hydroxide metalloporphyrin; magnesium meso-tetra-(4-N-methylpyridyl)-porphine; manganese meso-tetra-(4-N-methylpyridyl)-porphine; nickel meso-tetra(4-N-methylpyridyl)-porphine; nickel (II) meso-tetra(4-sulfonatophenyl)-porphine; palladium (II) meso-tetra-(4-N-methylpyridyl)-porphine; palladium meso-tetra-(4-N-methylpyridyl)-porphine; palladium tetraphenylporphyrin; palladium (II) meso(4-sulfonatophenyl)-porphine; platinum (II) meso(4-sulfonatophenyl)-porphine; samarium (II) dimethyltexaphyrin dihydroxide; silver (II) meso(4-sulfonatophenyl)-porphine; tin (IV) protoporphyrin; tin meso-tetra-(4-N-methylpyridyl)-porphine; tin meso-tetra(4-sulfonatophenyl)-porphine; tin (IV) tetrakis(4-sulfonatophenyl) porphyrin dichloride; zinc (II) 15-aza-3,7,12,18-tetramethyl-porphyrinato-13,17-diyl-dipropionic acid-dimethylester; zinc (II) chlorotexaphyrin chloride; zinc coproporphyrin III; zinc (II) 2,11,20,30-tetra-(1,1-dimethyl-ethyl)tetranaphtho(2,3-b:2',3'-g:2"3"-1:2"'3"'-q) porphyrazine; zinc (II) 2-(3-pyridyloxy)benzo[b]-10,19, 28-tri(1,1-dimethylethyl) trinaphtho[2',3'-g:2"3"1::2"',3"'-q] porphyrazine; zinc (II) 2,18-bis-(3-pyridyloxy)dibenzo[b,l]-10,26-di(1,1-dimethyl-ethyl)dinaphtho[2',3'-g:2"',3"'-q] porphyrazine; zinc (II) 2,9-bis-(3-pyridyloxy)dibenzo[b,g]-17,26-di(1,1-dimethyl-ethyl)dinaphtho[2"',3"-1:2"',3"'-q] porphyrazine; zinc (II) 2,9,16-tris-(3-pyridyloxy) tribenzo[b, g,l]-24=(1,1-dimethyl-ethyl)naphtho[2"',3"'-q] porphyrazine; zinc (II) 2,3-bis-(3-pyridyloxy)benzo[b]-10, 19,28-tri(1,1-dimethyl-ethyl)trinaphtho[2',3'-g:2",3"1:2"', 3"'-q]porphyrazine; zinc (II) 2,3,18,19-tetrakis-(3-pyridyloxy)dibenzo[b,l]-10,26-di(1,1-dimethyl-ethyl) trinaphtho[2',3'-g:2",3"'-q]porphyrazine; zinc (II) 2,3,9,10-tetrakis-(3-pyridyloxy)dibenzo[b,g]-17,26-di(1,1-dimethyl-ethyl)dinaphtho[2"',3"-1:2"',3"'-q]porphyrazine; zinc (II) 2,3, 9,10,16,17-hexakis-(3-pyridyloxy)tribenzo[b,g,l]-24-(1,1-dimethyl-ethyl)naphtho[2"',3"'-q]porphyrazine; zinc (II) 2-(3-N-methyl)pyridyloxy)benzo[b]-10,19,28-tri(1,1-dimethyl-ethyl)trinaphtho[2',3'-g:2",3"1:2"',3"'-q]porphyrazine monoiodide; zinc (II) 2,18-bis-(3-(N-methyl)pyridyloxy) dibenzo[b,l]-10,26-di(1,1-dimethylethyl)dinaphtho[2',3'-g: 2"',3"'-q]porphyrazine diiodide; zinc (II) 2,9-bis-(3-(N-methyl)pyridyloxy)dibenzo[b,g]-17,26-di(1,1-dimethylethyl) dinaphtho[2"',3"-1:2"',3"'-q]porphyrazine diiodide; zinc (II) 2,9,16-tris-(3-(N-methyl-pyridyloxy)tribenzo[b,g,l]-24-(1, 1-dimethylethyl)naphtho[2"',3"'-q]porphyrazine triiodide; zinc (II) 2,3-bis-(3-(N-methyl)pyridyloxy)benzo[b]-10,19, 28-tri(1,1-dimethylethyl)trinaphtho[2',3'-g:2",3"-1:2"',3"'-q] porphyrazine diiodide; zinc (II) 2,3,18,19-tetrakis-(3-(N-methyl)pyridyloxy)dibenzo[b,l]-10,26-di(1,1-dimethyl) dinaphtho[2',3'-g:2",3"'-q]porphyrazine tetraiodide; zinc (II) 2,3,9,10-tetrakis-(3-(N-methyl)pyridyloxy)dibenzo[g,g]-17, 26-di(1,1-dimethylethyl)dinaphtho[2",3"-1:2"',3"'-q]porphyrazine tetraiodide; zinc (II) 2,3,9,10,16,17-hexakis-(3-(N-methyl)pyridyloxy)tribenzo[b,g,l]-24-(1,1-dimethylethyl)naphtho[2"',3"'-q]porphyrazine hexaiodide; zinc (II) meso-diphenyl tetrabenzoporphyrin; zinc (II) meso-triphenyl tetrabenzoporphyrin; zinc (II) meso-tetrakis(2,6-dichloro-3-sulfonatophenyl) porphyrin; zinc (II) meso-tetra-(4-N-methylpyridyl)-porphine; zinc (II) 5,10,15,20-meso-tetra(4-octyl-phenylpropynyl)-porphine; zinc porphyrin c; zinc protoporphyrin; zinc protoporphyrin IX; zinc (II) meso-triphenyl-tetrabenzoporphyrin; zinc tetrabenzoporphyrin; zinc (II) tetrabenzoporphyrin; zinc tetranaphthaloporphyrin; zinc tetraphenylporphyrin; zinc (II) 5,10,15,20-tetraphenylporphyrin; zinc (II) meso (4-sulfonatophenyl)-porphine; and zinc (II) texaphyrin chloride.

Exemplary metallophthalocyanines include aluminum mono-(6-carboxy-pentyl-amino-sulfonyl)-trisulfo-phthalocyanine; aluminum di-(6-carboxy-pentyl-amino-sulfonyl)-trisulfophthalocyanine; aluminum (III) octa-n-butoxy phthalocyanine; aluminum phthalocyanine; aluminum (III) phthalocyanine disulfonate; aluminum phthalocyanine disulfonate; aluminum phthalocyanine disulfonate (cis isomer); aluminum phthalocyanine disulfonate (clinical prep.); aluminum phthalocyanine phthalimido-methyl sulfonate; aluminum phthalocyanine sulfonate; aluminum phthalocyanine trisulfonate; aluminum (III) phthalocyanine trisulfonate; aluminum (III) phthalocyanine tetrasulfonate; aluminum phthalocyanine tetrasulfonate; chloroaluminum phthalocyanine; chloroaluminum phthalocyanine sulfonate; chloroaluminum phthalocyanine disulfonate; chloroaluminum phthalocyanine tetrasulfonate; chloroaluminum-t-butyl-phthalocyanine; cobalt phthalocyanine sulfonate; copper phthalocyanine sulfonate; copper (II) tetra-carboxy-phthalocyanine; copper (II)-phthalocyanine; copper t-butyl-phthalocyanine; copper phthalocyanine sulfonate; copper (II) tetrakis-[methylene-thio[(dimethyl-amino)methylidyne]]phthalocyanine tetrachloride; dichlorosilicon phthalocyanine; gallium (III) octa-n-butoxy phthalocyanine; gallium (II) phthalocyanine disulfonate; gallium phthalocyanine disulfonate; gallium phthalocyanine tetrasulfonate-chloride; gallium (II) phthalocyanine tetrasulfonate; gallium phthalocyanine trisulfonate-chloride; gallium (II) phthalocyanine trisulfonate; GaPcS$_1$tBu$_3$; GaPcS$_2$tBu$_2$; GaPcS$_3$tBu$_1$; germanium (IV) octa-n-butoxy phthalocyanine; germanium phthalocyanine derivative; silicon phthalocyanine derivative; germanium (IV) phthalocyanine octakis-alkoxy-derivatives; iron phthalocyanine sulfonate; lead (II) 2,3,9,10,16,17,23,24-octakis(3,6-dioxaheptyloxy) phthalocyanine; magnesium t-butyl-phthalocyanine; nickel (II) 2,3,9,10,16,17,23,24-octakis(3,6-dioxaheptyloxy) phthalocyanine; palladium (II) octa-n-butoxy phthalocyanine; palladium (II) tetra(t-butyl)-phthalocyanine; (diol) (t-butyl)$_3$-phthalocyanato palladium (II); ruthenium(II) dipotassium[bis(triphenyl-phosphine-monosulphonate) phthalocyanine; silicon phthalocyanine bis(tri-n-hexyl-siloxy)-; silicon phthalocyanine bis(tri-phenyl-siloxy)-; HOSiPcOSi(CH$_3$)$_2$(CH$_2$)$_3$N(CH$_3$)$_2$; HOSiPcOSi(CH$_3$)$_2$(CH$_2$)$_3$N(CH$_2$CH$_3$)$_2$; SiPc[OSi(CH$_3$)$_2$(CH$_2$)$_3$N(CH$_3$)$_2$]$_2$; SiPc[OSi(CH$_3$)$_2$(CH$_2$)$_3$N(CH$_2$CH$_3$)(CH$_2$)$_2$N(CH$_3$)$_2$]$_2$; tin (IV) octa-n-butoxy phthalocyanine; vanadium phthalocyanine sulfonate; zinc (II) octa-n-butoxy phthalocyanine; zinc (II) 2,3,9,10,16,17,23,24-octakis(2-ethoxyethoxy) phthalocyanine; zinc (II) 2,3,9,10,16,17,23,24-octakis(3,6-dioxaheptyloxy)phthalocyanine; zinc (II) 1,4,8,11,15,18,22,25-octa-n-butoxy-phthalocyanine; zn(II)-phthalocyanine-octabutoxy; zn(II)-phthalocyanine; zinc phthalocyanine; zinc (II) phthalocyanine; zinc phthalocyanine and perdeuterated zinc phthalocyanine; zinc (II) phthalocyanine disulfonate; zinc phthalocyanine disulfonate; zinc phthalocyanine sulfonate; zinc phthalocyanine tetrabromo-; zinc (II) phthalocyanine tetra-t-butyl-; zinc (II) phthalocyanine tetra-(t-butyl)-; zinc phthalocyanine tetracarboxy-; zinc phthalocyanine tetrachloro-; zinc phthalocyanine tetrahydroxyl; zinc phthalocyanine tetraiodo-; zinc ((I) tetrakis-(1,1-dimethyl-2-phthalimido)ethyl phthalocyanine; zinc (II) tetrakis-(1,1-dimethyl-2-amino)-ethyl-phthalocyanine; zinc (II) phthalocyanine tetrakis(1,1-dimethyl-2-trimethyl ammonium)ethyl tetraiodide; zinc phthalocyanine tetrasulphonate; zinc phthalocyanine tetrasulfonate; zinc (II) phthalocyanine tetrasulfonate; zinc (II) phthalocyanine trisulfonate; zinc phthalocyanine trisulfonate; zinc (II) (t-butyl)$_3$-phthalocyanine diol; zinc tetradibenzobarreleno-octabutoxy-phthalocyanine; zinc (II) 2,9,16,23,-tetrakis-(3-(N-methyl)pyridyloxy) phthalocyanine tetraiodide; and zinc (II) 2,3,9,10,16,17,23,24-octakis-(3-(N-methyl)pyridyloxy)phthalocyanine complex octaiodide; and zinc (II) 2,3,9,10,16,17,23,24-octakis-(3-pyridyloxy)phthalocyanine.

Exemplary methylene blue derivatives include 1-methyl methylene blue; 1,9-dimethyl methylene blue; methylene blue; methylene blue (16 µM); methylene blue (14 µM; methylene violet; bromomethylene violet; 4-iodomethylene violet; 1,9-dimethyl-3-dimethyl-amino-7-diethyl-amino-phenothiazine; and 1,9-dimethyl-3-diethylamino-7-dibutyl-amino-phenothiazine.

Exemplary naphthalimides blue derivatives include N,N'-bis-(hydroperoxy-2-methoxyethyl)-1,4,5,8-naphthaldiimide; N-(hydroperoxy-2-methoxyethyl)-1,8-naphthalimide; 1,8-naphthalimide; N,N'-bis(2,2-dimethoxyethyl)-1,4,5,8-naphthaldiimide; and N,N'-bis(2,2-dimethylpropyl)-1,4,5,8-naphthaldiimide.

Exemplary naphthalocyanines include aluminum t-butyl-chloronaphthalocyanine; silicon bis(dimethyloctadecylsiloxy) 2,3-naphthalocyanine; silicon bis(dimethyloctadecylsiloxy) naphthalocyanine; silicon bis(dimethylthexylsiloxy) 2,3-naphthalocyanine; silicon bis(dimethylthexylsiloxy) naphthalocyanine; silicon bis(t-butyldimethylsiloxy) 2,3-naphthalocyanine; silicon bis(tert-butyldimethylsiloxy) naphthalocyanine; silicon bis(tri-n-hexylsiloxy) 2,3-naphthalocyanine; silicon bis(tri-n-hexylsiloxy) naphthalocyanine; silicon naphthalalocyanine; silicon naphthalocyanine; t-butylnaphthalocyanine; zinc (II) naphthalocyanine; zinc (II) tetraacetyl-amidonaphthalocyanine; zinc (II) tetraaminonaphthalocyanine; zinc (II) tetrabenzamidonaphthalocyanine; zinc (II) tetrahexylamidonaphthalocyanine; zinc (II) tetramethoxy-benzamidonaphthalocyanine; zinc (II) tetramethoxynaphthalocyanine; zinc naphthalocyanine tetrasulfonate; and zinc (II) tetradodecylamidonaphthalocyanine.

Exemplary nile blue derivatives include benzo[a]phenothiazinium, 5-amino-9-diethylamino-; benzo[a]phenothiazinium, 5-amino-9-diethylamino-6-iodo-; benzo[a]phenothiazinium, 5-benzylamino-9-diethylamino-; benzo[a]phenoxazinium, 5-amino-6,8-dibromo-9-ethylamino-; benzo[a]phenoxazinium, 5-amino-6,8-diiodo-9-ethylamino-; benzo[a]phenoxazinium, 5-amino-6-bromo-9-diethylamino-; benzo[a]phenoxazinium, 5-amino-9-diethylamino-(nile blue A); benzo[a]phenoxazinium, 5-amino-9-diethylamino-2,6-diiodo-; benzo[a]phenoxazinium, 5-amino-9-diethylamino-2,-iodo; benzo[a]phenoxazinium, 5-amino-9-diethylamino-6-iodo-; benzo[a]phenoxazinium, 5-benzylamino-9-diethylamino-(nile blue 2B); 5-ethylamino-9-diethylamino-benzo[a]phenoselenazinium chloride; 5-ethylamino-9-diethyl-aminobenzo[a]phenothiazinium chloride; and 5-ethylamino-9-diethyl-aminobenzo[a]phenoxazinium chloride.

Exemplary NSAIDs (nonsteroidal anti-inflammatory drugs) include benoxaprofen; carprofen; carprofen dechlorinated (2-(2-carbazolyl) propionic acid); carprofen (3-chloro-carbazole); chlorobenoxaprofen; 2,4-dichlorobenoxaprofen; cinoxacin; ciprofloxacin; decarboxy-ketoprofen; decarboxy-suprofen; decarboxy-benoxaprofen; decarboxy-tiaprofenic acid; enoxacin; fleroxacin; fleroxacin-N-oxide; flumequine; indoprofen; ketoprofen; lomefloxacin; 2-methyl-4-oxo-2H-1,2-benzothiazine-1,1-dioxide; N-demethyl fleroxacin; nabumetone; nalidixic acid; naproxen; norfloxacin; ofloxacin; pefloxacin; pipemidic acid; piroxicam; suprofen; and tiaprofenic acid.

Exemplary perylenequinones include hypericins such as hypericin; hypericin monobasic sodium salt; di-aluminum hypericin; di-copper hypericin; gadolinium hypericin; terbium hypericin, hypocrellins such as acetoxy hypocrellin A;

acetoxy hypocrellin B; acetoxy iso-hypocrellin A; acetoxy iso-hypocrellin B; 3,10-bis[2-(2-aminoethylamino)ethanol] hypocrellin B; 3,10-bis[2-(2-aminoethoxy)ethanol] hypocrellin B; 3,10-bis[4-(2-aminoethyl)morpholine] hypocrellin B; n-butylaminated hypocrellin B; 3,10-bis(butylamine) hypocrellin B; 4,9-bis(butylamine) hypocrellin B; carboxylic acid hypocrellin B; cystamine-hypocrellin B; 5-chloro hypocrellin A or 8-chloro hypocrellin A; 5-chloro hypocrellin B or 8-chloro hypocrellin B; 8-chloro hypocrellin B; 8-chloro hypocrellin A or 5-chloro hypocrellin A; 8-chloro hypocrellin B or 5-chloro hypocrellin B; deacetylated aldehyde hypocrellin B; deacetylated hypocrellin B; deacetylated hypocrellin A; deacylated, aldehyde hypocrellin B; demethylated hypocrellin B; 5,8-dibromo hypocrellin A; 5,8-dibromo hypocrellin B; 5,8-dibromo iso-hypocrellin B; 5,8-dibromo[1,12-CBr=CMeCBr(COMe)] hypocrellin B; 5,8-dibromo[1,12-CHBrC(=CH$_2$)CBr(COMe)] hypocrellin B; 5,8-dibromo[1-CH$_2$COMe, 12-COCOCH$_2$Br—] hypocrellin B; 5,8-dichloro hypocrellin A; 5,8-dichloro hypocrellin B; 5,8-dichlorodeacytylated hypocrellin B; 5,8-diiodo hypocrellin A; 5,8-diiodo hypocrellin B; 5,8-diiodo[1,12-CH=CMeCH (COCH$_2$I$_2$)—] hypocrellin B; 5,8-diiodo[1,12-CH$_2$C (CH$_2$I) =C(COMe)—] hypocrellin B; 2-(N,N-diethylamino) ethylaminated hypocrellin B; 3,10-bis[2-(N,N-diethylamino)-ethylamine]hypocrellin B; 4,9-bis[2-(N,N-diethylamino)-ethylamine] iso-hypocrellin B; dihydro-1,4-thiazine carboxylic acid hypocrellin B; dihydro-1,4-thiazine hypocrellin B; 2-(N,N-dimethylamino)propylamine hypocrellin B; dimethyl-1,3,5,8,10,12-hexamethoxy-4,9-perylenequinone-6,7-diacetate; dimethyl-5,8-dihydroxy-1,3,10,13-tetramethoxy-4,9-perylenequinone-6,7-diacetate; 2,11-dione hypocrellin A; ethanolamine hypocrellin B; ethanolamine iso-hypocrellin B; ethylenediamine hypocrellin B; 11-hydroxy hypocrellin B or 2-hydroxy hypocrellin B; hypocrellin A; hypocrellin B; 5-iodo[1,12-CH$_2$C(CH$_2$I)=C(COMe)—] hypocrellin B; 8-iodo[1,12-CH$_2$C(CH$_2$I)=C(COMe)—] hypocrellin B; 9-methylamino iso-hypocrellin B; 3,10-bis[2-(N,N-methylamino)propylamine]hypocrellin B; 4,9-bis(methylamine iso-hypocrellin B; 14-methylamine iso-hypocrellin B; 4-methylamine iso-hypocrellin B; methoxy hypocrellin A; methoxy hypocrellin B; methoxy iso-hypocrellin A; methoxy iso-hypocrellin B; methylamine hypocrellin B; 2-morpholino ethylaminated hypocrellin B; pentaacetoxy hypocrellin A; PQP derivative; tetraacetoxy hypocrellin B; 5,8,15-tribomo hypocrellin B; calphostin C, Cercosporins such as acetoxy cercosporin; acetoxy iso-cercosporin; aminocercosporin; cercosporin; cercosporin+iso-cercosporin (1/1 molar); diaminocercosporin; dimethylcercosporin; 5,8-dithiophenol cercosporin; iso-cercosporin; methoxycercosporin; methoxy iso-cercosporin; methylcercosporin; noranhydrocercosporin; elsinochrome A; elsinochrome B; phleichrome; and rubellin A.

Exemplary phenols include 2-benzylphenol; 2,2'-dihydroxybiphenyl; 2,5-dihydroxybiphenyl; 2-hydroxybiphenyl; 2-methoxybiphenyl; and 4-hydroxybiphenyl.

Exemplary pheophorbides include pheophorbide a; methyl 13$^1$-deoxy-20-formyl-7,8-vic-dihydro-bacterio-mesopheophorbide a; methyl-2-(1-dodecyloxyethyl)-2-devinyl-pyropheophorbide a; methyl-2-(1-heptyl-oxyethyl)-2-devinyl-pyropheophorbide a; methyl-2-(1-hexyl-oxyethyl)-2-devinyl-pyropheophorbide a; methyl-2-(1-methoxy-ethyl)-2-devinyl-pyropheophorbide a; methyl-2-(1-pentyl-oxyethyl)-2-devinyl-pyropheophorbide a; magnesium methyl bacteriopheophorbide d; methyl-bacteriopheophorbide d; and pheophorbide.

Exemplary pheophytins include bacteriopheophytin a; bacteriopheophytin b; bacteriopheophytin c; bacteriopheophytin d; 10-hydroxy pheophytin a; pheophytin; pheophytin a; and protopheophytin.

Exemplary photosensitizer dimers and conjugates include aluminum mono-(6-carboxy-pentyl-amino-sulfonyl)-trisulfophthalocyanine bovine serum albumin conjugate; dihematoporphyrin ether (ester); dihematoporphyrin ether; dihematoporphyrin ether (ester)-chlorin; hematoporphyrin-chlorin ester; hematoporphyrin-low density lipoprotein conjugate; hematoporphyrin-high density lipoprotein conjugate; porphine-2,7,18-tripropanoic acid, 13,13'-(1,3-propanediyl)bis[3,8,12,17-tetramethyl]-; porphine-2,7,18-tripropanoic acid, 13,13'-(1,11-undecanediyl)bis[3,8,12,17-tetramethyl]-; porphine-2,7,18-tripropanoic acid, 13,13'-(1,6-hexanediyl)bis[3,8,12,17-tetramethyl]-; SnCe6-MAb conjugate 1.7:1; SnCe6-MAb conjugate 1.7:1; SnCe6-MAb conjugate 6.8:1; SnCe6-MAb conjugate 11.2:1; SnCe6-MAb conjugate 18.9:1; SnCe6-dextran conjugate 0.9:1; SnCe6-dextran conjugate 3.5:1; SnCe6-dextran conjugate 5.5:1; SnCe6-dextran conjugate 9.9:1; α-terthienyl-bovine serum albumin conjugate (12:1); α-terthienyl-bovine serum albumin conjugate (4:1); and tetraphenylporphine linked to 7-chloroquinoline.

Exemplary phthalocyanines include (diol) (t-butyl)$_3$-phthalocyanine; (t-butyl)$_4$-phthalocyanine; cis-octabutoxy-dibenzo-dinaphtho-porphyrazine; trans-octabutoxy-dibenzo-dinaphtho-porphyrazine; 2,3,9,10,16,17,23,24-octakis2-ethoxyethoxy) phthalocyanine; 2,3,9,10,16,17,23,24-octakis(3,6-dioxaheptyloxy) phthalocyanine; octa-n-butoxy phthalocyanine; phthalocyanine; phthalocyanine sulfonate; phthalocyanine tetrasulphonate; phthalocyanine tetrasulfonate; t-butyl-phthalocyanine; tetra-t-butyl phthalocyanine; and tetradibenzobarreleno-octabutoxy-phthalocyanine.

Exemplary porphycenes include 2,3-(2$^3$-carboxy-2$^4$-methoxycarbonyl benzo)-7,12,17-tris(2-methoxyethyl)porphycene; 2-(2-hydroxyethyl)-7,12,17-tri(2-methoxyethyl) porphycene; 2-(2-hydroxyethyl)-7,12,17-tri-n-propyl-porphycene; 2-(2-methoxyethyl)-7,12,17-tri-n-propyl-porphycene; 2,7,12,17-tetrakis(2-methoxyethyl) porphycene; 2,7,12,17-tetrakis(2-methoxyethyl)-9-hydroxy-porphycene; 2,7,12,17-tetrakis (2-methoxyethyl)-9-methoxy-porphycene; 2,7,12,17-tetrakis(2-methoxyethyl)-9-n-hexyloxy-porphycene; 2,7,12,17-tetrakis(2-methoxyethyl)-9-acetoxy-porphycene; 2,7,12,17-tetrakis(2-methoxyethyl)-9-caproyloxy-porphycene; 2,7,12,17-tetrakis (2-methoxyethyl)-9-pelargonyloxy-porphycene; 2,7,12,17-tetrakis(2-methoxyethyl)-9-stearoyloxy-porphycene; 2,7,12,17-tetrakis(2-methoxyethyl)-9-(N-t-butoxycarbonylglycinoxy) porphycene; 2,7,12,17-tetrakis (2-methoxyethyl)-9-[4-((β-apo-7-carotenyl)benzoyloxyl-porphycene; 2,7,12,17-tetrakis(2-methoxyethyl)-9-amino-porphycene; 2,7,12,17-tetrakis(2-methoxyethyl)-9-acetamido-porphycene; 2,7,12,17-tetrakis(2-methoxyethyl)-9-glutaramido-porphycene; 2,7,12,17-tetrakis(2-methoxyethyl)-9-(methyl-glutaramido)-porphycene; 2,7,12,17-tetrakis(2-methoxyethyl)-9-(glutarimido)-porphycene; 2,7,12,17-tetrakis(2-methoxyethyl)-3-(N,N-dimethylaminomethyl)-porphycene; 2,7,12,17-tetrakis; (2-methoxyethyl)-3-(N,N-dimethylaminomethyl)-porphycene hydrochloride; 2,7,12,17-tetrakis (2-ethoxyethyl)-porphycene; 2,7,12,17-tetra-n-porphycene; 2,7,12,17-tetra-n-propyl-9-hydroxy-porphycene; 2,7,12,17-tetra-n-propyl-9-methoxy-porphycene; 2,7,12,17-tetra-n-propyl-9-acetoxy porphycene; 2,7,12,17-tetra-n-propyl-9-(t-butyl glutaroxy)-porphycene; 2,7,12,17-tetra-n-propyl-9-(N-t- butoxycarbonylglycinoxy)-porphycene; 2,7,12,17-tetra-n-propyl-9-(4-N-t-butoxy-carbonyl-butyroxy)-porphycene; 2,7,12,17-tetra-n-propyl-9-amino-porphycene; 2,7,12,17-tetra-n-propyl-9-acetamido-porphycene; 2,7,12,17-tetra-n-propyl-9-glutaramido-porphycene; 2,7,12,17-tetra-n-propyl-9-(methyl glutaramido)-porphycene; 2,7,12,17-tetra-n-propyl-3-(N,N-dimethylaminomethyl) porphycene; 2,7,12, 17-tetra-n-propyl-9,10-benzo porphycene; 2,7,12,17-tetra-n-propyl-9-p-benzoyl carboxy-porphycene; 2,7,12,17-tetra-n-propyl-porphycene; 2,7,12,17-tetra-t-butyl-3,6;13,16-dibenzo-porphycene; 2,7-bis(2-hydroxyethyl)-12,17-di-n-propyl-porphycene; 2,7-bis(2-methoxyethyl)-12,17-di-n-propyl-porphycene; and porphycene.

Exemplary porphyrins include 5-azaprotoporphyrin dimethylester; bis-porphyrin; coproporphyrin III; coproporphyrin III tetramethylester; deuteroporphyrin; deuteroporphyrin IX dimethylester; diformyldeuteroporphyrin IX dimethylester; dodecaphenylporphyrin; hematoporphyrin; hematoporphyrin (8 µM); hematoporphyrin (400 µM); hematoporphyrin (3 µM); hematoporphyrin (18 µM); hematoporphyrin (30 µM); hematoporphyrin (67 µM); hematoporphyrin (150 µM); hematoporphyrin IX; hematoporphyrin monomer; hematoporphyrin dimer; hematoporphyrin derivative; hematoporphyrin derivative (6 µM); hematoporphyrin derivative (200 µM); hematoporphyrin derivative A (20 µM); hematoporphyrin IX dihydrochloride; hematoporphyrin dihydrochloride; hematoporphyrin IX dimethylester; haematoporphyrin IX dimethylester; mesoporphyrin dimethylester; mesoporphyrin IX dimethylester; monofonnyl-monovinyl-deuteroporphyrin IX dimethylester; monohydroxyethylvinyl deuteroporphyrin; 5,10,15,20-tetra (o-hydroxyphenyl)porphyrin; 5,10,15,20-tetra(m-hydroxyphenyl)porphyrin; 5,10,15,20-tetrakis-(m-hydroxyphenyl) porphyrin; 5,10,15,20-tetra(p-hydroxyphenyl)porphyrin; 5,10,15,20-tetrakis(3-methoxyphenyl) porphyrin; 5,10,15, 20-tetrakis(3,4-dimethoxyphenyl) porphyrin; 5,10,15,20-tetrakis(3,5-dimethoxyphenyl) porphyrin; 5,10,15,20-tetrakis (3,4,5-trimethoxyphenyl) porphyrin; 2,3,7,8,12,13,17,18-octaethyl-5,10,15,20-tetraphenylporphyrin; Photofrin®; Photofrin® II; porphyrin c; protoporphyrin; protoporphyrin IX; protoporphyrin dimethylester; protoporphyrin IX dimethylester; protoporphyrin propylaminoethylformamide iodide; protoporphyrin N,N-dimethylaminopropylformamide; protoporphyrin propylaminopropylformamide iodide; protoporphyrin butylformamide; protoporphyrin N,N-dimethylamino-formamide; protoprophyrin formamide; sapphyrin 1 3,12,13,22-tetraethyl-2,7,18,23 tetramethyl sapphyrin-8,17-dipropanol; sapphyrin 2 3,12,13,22-tetraethyl-2,7,18, 23 tetramethyl sapphyrin-8-monoglycoside; sapphyrin 3; meso-tetra-(4-N-carboxyphenyl)-porphine; tetra-(3-methoxyphenyl)-porphine; tetra-(3-methoxy-2,4-difluorophenyl)-porphine; 5,10,15,20-tetrakis(4-N-methylpyridyl) porphine; meso-tetra-(4-N-methylpyridyl)-porphine tetrachloride; meso-tetra(4-N-methylpyridyl)-porphine; meso-tetra-(3-N-methylpyridyl)-porphine; meso-tetra-(2-N-methylpyridyl)-porphine; tetra(4-N,N,N-trimethylanilinium) porphine; meso-tetra-(4-N,N,N"-trimethylamino-phenyl) porphine tetrachloride; tetranaphthaloporphyrin; 5,10,15,20-tetraphenylporphyrin; tetraphenylporphyrin; meso-tetra-(4-N-sulfonatophenyl)-porphine; tetraphenylporphine tetrasulfonate; meso-tetra(4-sulfonatophenyl)porphine; tetra(4-sulfonatophenyl)porphine; tetraphenylporphyrin sulfonate; meso-tetra(4-sulfonatophenyl)porphine; tetrakis(4-sulfonatophenyl)porphyrin; meso-tetra(4-sulfonatophenyl)porphine; meso(4-sulfonatophenyl)porphine; meso-tetra(4-sulfonatophenyl)porphine; tetrakis(4-sulfonatophenyl) porphyrin; meso-tetra(4-N-trimethylanilinium)-porphine; uroporphyrin; uroporphyrin I (17 µM); uroporphyrin IX; and uroporphyrin I (18 µM).

Exemplary psoralens include psoralen; 5-methoxypsoralen; 8-methoxypsoralen; 5,8-dimethoxypsoralen; 3-carbethoxypsoralen; 3-carbethoxy-pseudopsoralen; 8-hydroxypsoralen; pseudopsoralen; 4,5',8-trimethylpsoralen; allopsoralen; 3-aceto-allopsoralen; 4,7-dimethyl-allopsoralen; 4,7,4'-trimethyl-allopsoralen; 4,7,5'-trimethyl-allopsoralen; isopseudopsoralen; 3-acetoisopseudopsoralen; 4,5'-dimethyl-isopseudopsoralen; 5',7-dimethyl-isopseudopsoralen; pseudoisopsoralen; 3-acetopseudoisopsoralin; 3/4',5'-trimethyl-aza-psoralen; 4,4',8-trimethyl-5'-amino-methylpsoralen; 4,4',8-trimethyl-phthalamyl-psoralen; 4,5',8-trimethyl-4'-aminomethyl psoralen; 4,5',8-trimethyl-bromopsoralen; 5-nitro-8-methoxy-psoralen; 5'-acetyl-4,8-dimethyl-psoralen; 5'-aceto-8-methyl-psoralen; and 5'-aceto-4,8-dimethyl-psoralen.

Exemplary purpurins include octaethylpurpurin; octaethylpurpurin zinc; oxidized octaethylpurpurin; reduced octaethylpurpurin; reduced octaethylpurpurin tin; purpurin 18; purpurin-18; purpurin-18-methyl ester; purpurin; tin ethyl etiopurpurin I; Zn(II) aetio-purpurin ethyl ester; and zinc etiopurpurin.

Exemplary quinones include 1-amino-4,5-dimethoxy anthraquinone; 1,5-diamino-4,8-dimethoxy anthraquinone; 1,8-diamino-4,5-dimethoxy anthraquinone; 2,5-diamino-1, 8-dihydroxy anthraquinone; 2,7-diamino-1,8-dihydroxy anthraquinone; 4,5-diamino-1,8-dihydroxy anthraquinone; mono-methylated 4,5- or 2,7-diamino-1,8-dihydroxy antraquinone; anthralin (keto form); anthralin; anthralin anion; 1,8-dihydroxy anthraquinone; 1,8-dihydroxy anthraquinone (Chrysazin); 1,2-dihydroxy anthraquinone; 1,2-dihydroxy anthraquinone (Alizarin); 1,4-dihydroxy anthraquinone (Quinizarin); 2,6-dihydroxy anthraquinone; 2,6-dihydroxy anthraquinone (Anthraflavin); 1-hydroxy anthraquinone (Erythroxy-anthraquinone); 2-hydroxy-anthraquinone; 1,2,5,8-tetra-hydroxy anthraquinone (Quinalizarin); 3-methyl-1,6,8-trihydroxy anthraquinone (Emodin); anthraquinone; anthraquinone-2-sulfonic acid; benzoquinone; tetramethyl benzoquinone; hydroquinone; chlorohydroquinone; resorcinol; and 4-chlororesorcinol.

Exemplary retinoids include all-trans retinal; $C_{17}$ aldehyde; $C_{22}$ aldehyde; 11-cis retinal; 13-cis retinal; retinal; and retinal palmitate.

Exemplary rhodamines include 4,5-dibromo-rhodamine methyl ester; 4,5-dibromo-rhodamine n-butyl ester; rhodamine 101 methyl ester; rhodamine 123; rhodamine 6G; rhodamine 6G hexyl ester; tetrabromo-rhodamine 123; and tetramethyl-rhodamine ethyl ester.

Exemplary thiophenes include terthiophenes such as 2,2': 5',2"-terthiophene; 2,2':5',2"-terthiophene-5-carboxamide; 2,2':5',2"-terthiophene-5-carboxylic acid; 2,2':5',2"-terthiophene-5-L-serine ethyl ester; 2,2':5',2"-terthiophene-5-N-isopropynyl-formamide; 5-acetoxymethyl-2,2':5',2"-terthiophene; 5-benzyl-2,2':5',2"-terthiophene-sulphide; 5-benzyl-2,2':5',2"-terthiophene-sulfoxide; 5-benzyl-2,2':5', 2"-terthiophene-sulphone; 5-bromo-2,2':5',2"-terthiophene; 5-(butynyl-3'''-hydroxy)-2,2':5',2"-terthiophene; 5-carboxyl-5"-trimethylsilyl-2,2':5',2"-terthiophene; 5-cyano-2,2':5',2"-terthiophene; 5,5"-dibromo-2,2':5',2"-terthiophene; 5-(1''', 1'''-dibromoethenyl)-2,2':5',2"-terthiophene; 5,5"-dicyano-2, 2':5',2"-terthiophene; 5,5l-diformyl-2,2':5',2"-terthiophene; 5-difluoromethyl-2,2':5',2"-terthiophene; 5,5"-diiodo-2,2':5', 2"-terthiophene; 3,3"-dimethyl-2,2':5',2"-terthiophene; 5,5"-dimethyl-2,2':5',2"-terthiophene; 5-(3''',3'''-dimethylacryloyloxymethyl)-2,2':5',2"-terthiophene; 5,5"-di-(t-butyl)-2,2':5', 2"-terthiophene; 5,5"-dithiomethyl-2,2':5',2"-terthiophene; 3'-ethoxy-2,2':5',2"-terthiophene; ethyl 2,2':5',2"-terthiophene-5-carboxylic acid; 5-formyl-2,2':5',2"-terthiophene; 5-hydroxyethyl-2,2':5',2"-terthiophene; 5-hydroxymethyl-2,2':5',2"-terthiophene; 5-iodo-2,2':5',2"-terthiophene; 5-methoxy-2,2':5',2"-terthiophene; 3'-methoxy-2,2':5',2"-terthiophene; 5-methyl-2,2':5',2"-terthiophene; 5-(3"'-methyl-2"'-butenyl)-2,2':5',2"-terthiophene; methyl 2,2':5',2"-terthiophene; 5-[3"'-acrylate]; methyl 2,2':5',2"-terthiophene-5-(3"'-propionate); N-allyl-2,2':5',2"-terthiophene-5-sulphonimide; N-benzyl-2,2':5',2"-terthiophene-5-sulphonamide; N-butyl-2,2':5',2"-terthiophene-5-sulfonimide; N,N-diethyl-2,2':5',2"-terthiophene-5-sulphonimide; 3,3',4',3"-tetramethyl-2,2':5',2"-terthiophene; 5-t-butyl-5"-trimethylsilyl-2,2':5',2"-terthiophene; 3'-thiomethyl-2,2':5',2"-terthiophene; 5-thiomethyl-2,2':5',2"-terthiophene; 5-trimethylsilyl-2,2':5',2"-terthiophene; bithiophenes such as 2,2'-bithiophene; 5-cyano-2,2'-bithiophene; 5-formyl-2,2'-bithiophene; 5-phenyl-2,2'-bithiophene; 5-(propynyl)-2,2'-bithiophene; 5-(hexynyl)-2,2'-bithiophene; 5-(octynyl)-2,2'-bithiophene; 5-(butynyl-4"-hydroxy)-2,2'-bithiophene; 5-(pentynyl-5"-hydroxy)-2,2'-bithiophene; 5-(3",4"-dihydroxybutynyl)-2,2'-bithiophene derivative; 5-(ethoxybutynyl)-2,2'-bithiophene deriative, and miscellaneous thiophenes such as 2,5-diphenylthiophene; 2,5-di(2-thienyl)furan; pyridine,2,6-bis(2-thienyl)-; pyridine, 2,6-bis(thienyl)-; thiophene, 2-(1-naphthalenyl)-; thiophene, 2-(2-naphthalenyl)-; thiophene, 2,2'-(1,2-phenylene)bis-; thiophene, 2,2'-(1,3-phenylene)bis-; thiophene, 2,2'-(1,4-phenylene) bis-; 2,2':5',2":5",2"'-quaterthiophene; α-quaterthienyl; α-tetrathiophene; α-pentathiophene; α-hexathiophene; and α-heptathiophene.

Exemplary verdins include copro (II) verdin trimethyl ester; deuteroverdin methyl ester; mesoverdin methyl ester; and zinc methyl pyroverdin.

Exemplary vitamins include ergosterol (provitamin D2); hexamethyl-Co a Co b-dicyano-7-de(carboxymethyl)-7,8-didehydro-cobyrinate (Pyrocobester); pyrocobester; and vitamin D3.

Exemplary xanthene dyes include Eosin B (4',5'-dibromo, 2',7'-dinitro-flourescein, dianion); eosin Y; eosin Y (2',4',5',7'-tetrabromo-fluorescein, dianion); eosin (2',4',5',7'-tetrabromo-fluorescein, dianion); eosin (2',4',5',7'-tetrabromo-fluorescein, dianion) methyl ester; eosin (2',4',5',7'-tetrabromo-fluorescein, monoanion) p-isopropylbenzyl ester; eosin derivative (2',7'-dibromo-fluorescein, dianion); eosin dirivative (4',5'-dibromo-fluorescein, dianion); eosin derivative (2',7'-dichloro-flourescein, dianion); eosin derivative (4',5'-dichloro-fluorescein, dianion); eosin derivative (2',7'-diiodo-fluorescein, dianion); eosin derivative (4',5'-diiodo-fluorescein, dianion); eosin derivative (tribromo-fluorescein, dianion); eosin derivative (2',4',5',7'-tetrachloro-flourescein, dianion); eosin; eosin dicetylpyridinium chloride ion pair; erythrosin B (2',4',5',7'-tetraiodo-fluorescein, dianion); erythrosin; erythrosin dianion; erythrosin B; fluorescein; fluorescein dianion; phloxin B (2',4',5',7'-tetrabromo-3,4,5,6-tetrachloro-flourescein, dianion); phloxin B (tetrachloro-tetrabromo-fluorescein); phloxine B; rose bengal (3,4,5,6-tetrachloro-2',4',5',7'-tetraiodofluorescein, dianion); rose bengal; rose bengal dianion; rose bengal O-methyl-methyl-ester; rose bengal 6'-O-acetyl ethyl ester; rose bengal benzyl ester diphenyl-diiodonium salt; rose bengal benzyl ester triethylammonium salt; rose bengal benzyl ester, 2,4,6,-triphenylpyrilium salt; rose bengal benzyl ester, benzyltriphenylphosphonium salt; rose bengal benzyl ester, benzyltriphenyl phosphonium salt; rose bengal benzyl ester, diphenyl-iodonium salt; rose bengal benzyl ester, diphenyl-methylsulfonium salt; rose bengal benzyl ester, diphenyl-methyl-sulfonium salt; rose bengal benzyl ester, triethyl-ammonium salt; rose bengal benzyl ester, triphenyl pyrilium; rose bengal bis (triethyl-ammonium) salt) (3,4,5,6-tetrachloro-2',4',5',7'-tetraiodofluorescein, bis(triethyl-ammonium salt); rose bengal bis (triethyl-ammonium) salt; rose bengal bis(benzyl-triphenyl-phosphonium) salt (3,4,5,6-tetrachloro-2',4',5',7'-tetraiodofluorescein, bis(benzyl-triphenyl-phosphonium) salt); rose bengal bis(diphenyl-iodonium) salt (3,4,5,6-tetrachloro-2',4',5',7'-tetraiodofluorescein, bis(diphenyl-iodonium) salt); rose bengal di-cetyl-pyridinium chloride ion pair; rose bengal ethyl ester triethyl ammonium salt; rose bengal ethyl ester triethyl ammonium salt; rose bengal ethyl ester; rose bengal methyl ester; rose bengal octyl ester tri-n-butyl-ammonium salt RB; rose bengal, 6'-O-acetyl-, and ethyl ester.

Typically, the photosensitizing agent can be formulated into a pharmaceutical composition by mixing the photosensitizing agent, typically at ambient temperatures, appropriate pH's, and the desired degree of purity, with one or more physiologically acceptable carriers, i.e., carriers that are non-toxic to recipients at the dosages and concentrations employed. Suitable compositions include those appropriate for systemic or topical administration, including preparations for injection, transmucosal administration, transdermal administration or intravitreal administration.

Treatment with low dose PDT may be combined with treatment with one or more immunosuppressive agents to enhance the anti-inflammatory effect on the target tissue. Examples of such agents include, but are not limited to, 2-amino-6-aryl-5-substituted pyrimidines; azathioprine or cyclophosphamide; bromocryptine; glutaraldehyde; anti-idiotypic antibodies for MHC antigens; cyclosporin A; one or more steroids, preferably corticosteroids and glucocorticosteroids such as prednisone, methyl prednisolone, and dexamethasone; anti-interferon-gamma antibodies; anti-tumor necrosis factor-alpha antibodies; anti-tumor necrosis factor-beta antibodies; anti-interleukin-2 antibodies; anticytokine receptor antibodies such as anti-IL-2 receptor antibodies; heterologous anti-lymphocyte globulin; pan-T antibodies, preferably OKT-3 monoclonal antibodies; antibodies to CD4; streptokinase; streptodomase; or RNA or DNA from the host.

This immunosuppressive agent may be administered simultaneously or separately, systemically or locally. The effective amount of such other agents is subject to a great deal of therapeutic discretion and depends on the amount of the photosensitizing agent present in the formulation, the type of injury, the type of immunosuppressive agent, the site of delivery, the method of administration, the scheduling of administration, other factors discussed above, and other factors known to practitioners. However, the amount of immunosuppressive agent appropriate for use with the invention is typically lower than that normally advisable for the treatment of like target tissues.

When an immunosuppressive agent is used, it may be administered by any suitable means, including parenteral and, if desired for local immunosuppressive treatment, intralesionally, i.e., topically to the target tissues. Parenteral infusions include intramuscular, intravenous, intraarterial, intraperitoneal, subcutaneous, and subconjunctival administration.

In addition to anti-inflammatory drugs, anti-angiogenic agents or neuroprotective agents can also be used in conjunction with low dose PDT. Exemplary neuroprotective compounds include free radical scavengers, e.g., Ebselen, Tirilazad, ganglioside, citicholine and vitamin E, GABA agonist, e.g., Clomethiazole, Ca channel antagonist, e.g., Nimodipine and Flunarizine, K channel agonist, e.g., BMS- 204352, Na Channel antagonist, e.g., Fosphenytoin, and glutamate receptor antagonist, e.g., Eliprodil, Cerestat and Selfotel. Exemplary anti-angiogenic compounds include matrix metalloproteinase inhibitor, e.g., AG3340 and marimastat, integrin antagonist, e.g., EMD121974 and Vitaxin, PKC inhibitor, e.g., PKC412 and LY 333531, VEGF receptor antagonist, e.g., CEP-5214, ZD4190, SU5416 and c-p1C11, angiostatic steroid, e.g., squalamine and anecortave acetate, somatostatin analog, anti VEGF, e.g., NX1838 and Genentech rhMAb anti-VEGF, and other molecules such as thalidomide, IM862, angiozyme, endostatin, angiostatin, shark cartilage extracts, e.g., BeneFin and AE-941 and TNP-470.

C. The Normal Dose PDT

The subject of the current invention treatment will have been treated with normal dose PDT using methods known in the art. The subject has been administered an amount of the photosensitizing agent, or a mixture of photosensitizing agents, in one or several dosages. The photosensitizing agents are dosed in a fashion consistent with good medical practice, taking into account the nature of the disease being prevented or reduced, the species and medical condition of the subject, the presence of any other drug in the subject's body, the purity and chemical form of the photosensitizer, the mode of administration, the rate and degree of absorption expected, and other factors known to practitioners. The therapeutic dose, i.e., the normal dosage, is an amount of the photosensitizing agent that causes destruction of tumor cells or neovasculature upon appropriate light irradiation.

As is known, the dose of the photosensitizing agent will vary with the target tissue and, if administered intravenously or systemically, will be limited by the weight and optimal blood level of the subject. Suitable systemic amounts per dose are typically less than about 10 mg/kg of body weight, preferably in the range of from about 1 to 5 mg/kg per dose and, most preferably, about 2 mg/kg per dose. These dosage ranges are intended to be suggestive and should not necessarily be considered as limiting, since the individual reactions of particular subjects will also vary.

Depending on the photosensitizing agent and the mode of administration, an equivalent optimal systemic blood level can be established, but it is difficult to do because the photosensitizer preferably clears very rapidly. Thus, there can be a dramatic difference between the concentration of the photosensitizer in the bloodstream at the moment of injection and the concentration at the time of treatment with light. For example, the concentration of BPD at the moment of intravenous injection may range from about 1-10 mg/mL, while, at the time of light exposure, may only be in the range of from about 0.5-0.05 ug/mL. If by topical administration, no photosensitizer at all is typically detectable in the blood.

When administered topically, the dose is best described in terms of the concentration of the composition and the length of the time of contact with the target tissue. A generally effective range of concentrations for the photosensitizing agent is from about 0.1 to about 10 mg/mL, preferably from about 0.1 to about 5 mg/mL and, most preferably, from about 0.25 to about 2.0 mg/ml. The contact suitably involves applying the composition to one or more surfaces of the target tissue with the pharmaceutical composition of the invention. Topical contact with the photosensitizer generally takes place for at least one minute, preferably under five minutes, and even more preferably from about one to two minutes. The time of contact depends on such factors as the concentration of the photosensitizing agent in the composition, the tissue to be treated, and the particular type of composition.

In one specific embodiment, verteporfin is used for treating choridal neovasculature. The dosage of vertepofrin may be about 6 mg/m$^2$ body surface area, followed by 50 J/cm$^2$ of 689 nm laser light. When tin ethyl etiopurpurin is used for treating choridal neovasculature, the dosage of tin ethyl etiopurpurin may be about 0.5-0.75 mg/kg drug (i.v.) and followed by 36 J/cm$^2$ of 664 nm laser light. When motexafin luthetium is used for treating choridal neovasculature, the dosage of motexafin luthetium may be about 2.0 mg/kg of drug (i.v.) and followed by 50-95 J/cm$^2$ of 732 nm laser light. Following the step of bringing the target tissue into contact with a composition containing the photosensitizer, the tissue is subjected to exposure with normal dose light having a wavelength that is absorbed by the photosensitizing agent and leads to the intended preventive or therapeutic effect. The exposure to the normal dose light is followed, according to the present invention, by exposure with low dose light having a wavelength that is absorbed by the photosensitizing agent and leads to the prevention or reduction of the inflammation arising from normal dose PDT treatment.

D. Low Dose PDT to Prevent or Reduce Inflammation

To effectively reduce or prevent inflammation caused by normal dose PDT treatment of a target tissue, the target tissue should be subjected to low dose light radiation soon after the target tissue has been treated with the normal dose PDT. The target tissue may be subjected to low dose light radiation immediately after the target tissue has been treated with the normal dose PDT. Preferably, the time gap between the low dose and the normal dose radiation is from immediately after to several hours after normal dose light radiation, preferably from immediately to about 15 minutes after normal dose light radiation.

The dosage and exposing time of the low dose PDT treatment can be decided, e.g., empirically, in view of the subject treated with the normal dose PDT treatment, the location of the target tissue in the subject, the dosage of the photosensitizing agent delivered to the target tissue, and the dosage and exposing time of the preceding normal dose PDT treatment. Because the total PDT dose depends on a combination of the dose of the photosensitizing agent and the dose of the irradiating light, low-dose PDT may be administered in combinations of relatively high photosensitizer doses and low light doses or, on the other hand, combinations of relatively low photosensitizer doses and relatively high light doses. The latter low photosensitizer/high light combination can also be achieved by administering a relatively normal dose of photosensitizer, followed by an unusually long "clearance" time before being irradiated with light. Therefore, a wide variety of conditions, all producing a relatively low dose of PDT overall, would be suitable for the invention.

Likewise, a wide variety of different combinations of photosensitizer doses, contact times, and modes of administration are suitable. However, the following rough guidelines may be useful. Short contact (less than one hour) with normal doses of the photosensitizer, e.g., 2 mg/mL applied topically, would generally be equivalent to a low photosensitizer dose, e.g., 0.15 mg/kg administered intravenously. However, even after a normal dose of photosensitizer administered intravenously, delaying irradiation with light to a later time, e.g., more than three hours, after administration of the photosensitizing agent can also result in low-dose PDT because, if the photosensitizer is capable of rapid clearance, very little of it may still be present in the tissues after three hours.

For irradiation with low dose light, the fluence rate of the light source should not exceed 600 mW/cm$^2$, the total dosage of irradiation should not exceed 100 J/cm$^2$, and the exposing time should not exceed 2 minutes. For example, the dosage of the low dose light is from about 1 J/cm$^2$ to about 10, to about 15, to about 20, to about 25, or to about 50 J/cm$^2$. Preferably, the dosage of the low dose light is about 1, about 2, about 3, about 4, about 5, about 6, about 7, about 8, about 9, about 10, about 12, about 14, or about 15 J/cm$^2$. The low dose irradiation lasts from about 1 second to about 15 minutes or from about 10 seconds to about 15 minutes. Preferably, the low dose irradiation lasts from about 1 second to about 60 seconds. More preferably, the low dose irradiation lasts about 5, about 10, about 15, about 20, or about 25 seconds.

In general, the area exposed to low dose PDT should overlap with, and sometimes may be, larger than the area exposed radiation under normal dose PDT. Preferable, the entire area exposed to the normal dose PDT is included in the low dose treatment. Also preferably, the area exposed to the low dose light in the target tissue should be concentric with but larger than the area exposed to the normal dose PDT treatment. The area exposed to the low dose light is at least about 1 or 1.5-10 times, preferably, 1-3 times of the area exposed to the normal dose PDT treatment.

The area treated with low dose PDT may thus include any cell or tissue adjacent to the area treated with normal dose PDT. This includes, but is not limited to, an area that is about 1.1, 1.2, 1.3, 1.4, 1.5, 1.6, 1.7, 1.8, 1.9, 2, 2.2, 2.4, 2.6, 2.8, 3, 3.2, or 3.4 times the area treated with normal dose PDT. Thus for a circle of 5 mm containing a lesion treated with normal dose PDT, low dose PDT may be subsequently applied to an area slightly larger than a 5 mm circle to about 3 times the size of a 5 mm circle. As will be appreciated by those skilled in the art, the initial area treated with normal PDT is determined by the size of the lesion to be treated and the judgement of the skilled practitioner.

The wavelength of the light source should be within a range absorbed by the photosensitizing agents used in the normal dose irradiation. During the irradiation step, any light that the photosensitizer absorbs and that is appropriate for use with the target tissue may be used, e.g., from about 380 to about 850 nm, depending upon the photosensitizer and upon the depth of tissue penetration desired, preferably from about 400 to about 750 nm, e.g., 689 nm. For general anti-inflammatory applications, light in the visible portion of the electromagnetic spectrum, e.g., red light, blue light or even UVA light, may be used. Light having a wavelength shorter than 400 nm is acceptable, but not preferred because of the potentially damaging effects of UVA light. Light having a wavelength longer than 700 nm is also acceptable, but not particularly preferred because it is difficult to see, thus making the visual control of irradiation more difficult. For ocular applications, red light is preferred because this eliminates any potentially harmful effects from the blue and UVA spectral ranges on the sensitive retina of the eye.

The spectra for the photosensitizing agents described above, as well as wavelengths required for activation of these agents are known in the art. For any particular photosensitizing agent, it is a trivial matter to ascertain the spectrum. For green porphyrins, as discussed above, the desired wavelength range is generally between about 550 and 695 nm. A wavelength in this range is especially preferred for enhanced penetration into bodily tissues. Preferred wavelengths for the practice of the invention are at about 685-695 nm, particularly at about 686, about 687, about 688, about 689, about 690, about 691, and about 692 nm.

Photosensitizing agent spectra, as well as wavelengths for their activation, have been described in the art. Irradiation of the administered photosensitizer is preferably with light containing a wavelength absorbed by the photosensitizer selected.

In one preferred embodiment of the invention, low dose PDT may be administered immediately following, or almost immediately following, administration of normal PDT by increasing the size of the spot undergoing irradiation. The increased spot size preferably defines a concentric circle relative to the circular spot in which normal PDT occurred. Such a concentric circle would necessarily contain cells and tissues previously not subjected to PDT treatment. While the fluence rate may be reduced simultaneously with the increase in spot size, the rate may also be maintained at a constant level. Irradiation for a short period of time, such as, but not limited to, about 1, about 5, about 10, about 15, about 20, or about 25 seconds would result in the delivery of a low light dose relative to the preceding PDT treatment to deliver normal dose PDT, which would have occurred via irradiation for longer time intervals to result in the delivery of higher light doses.

The following example is included for illustrative purposes only and is not intended to limit the scope of the invention.

E. Examples

Materials and Methods

Animal Model

Twelve pigmented rabbits weighing between 2 and 4 kg were used. Animals were anesthetized with ketamine HCI (40 mg/kg) and xylocaine (5 mg/kg). Tetracaine HCI (0.5%) was used for topical anesthesia. Tropicamide (1%) and phenylephrine (2.5%) eye drops were used for pupillary dilation. Euthanasia was accomplished with sodium pentobarbital (150 mg/kg) intracardiac injection. Two rabbits were sacrificed at day 2, 7, 14, 28, 42 and 56 following PDT.

PDT

Ten rabbits were injected intravenously with 2 mg/kg BPD-MA, and 689 nm laser light at 600 mW/cm$^2$ was successively applied on three 1.25-mm spot in one eye according to the following schedule:

| Time post PDT | Dose of Light | Time of irradiation |
|---|---|---|
| 15 min | 75 J/cm$^2$ | 2 min 5 sec |
| 20 min | 100 J/cm$^2$ | 2 min 47 sec |
| 25 min | 150/Jcm$^2$ | 4 min 10 sec |

Following PDT, animals were kept in a dark room overnight.

Photography

Fluorescein angiography (FA) and fundus photography were performed as 2 baseline before PDT, the day after PDT, weekly, and at the day of sacrifice.

Histological Preparation

All eyes were enucleated immediately after euthanasia. After the cornea, lens, and vitreous were removed, experimental area was delineated with sharp cuts. Tissue was placed in freezing compound (OCT) and frozen in liquid nitrogen. Serial cryosections were cut and stored at −70° C. Non-treated eyes were used for control. Cryosections were stained with H&E and immunohistochemical staining.

Immunohistochemistry

Monoclonal antibodies to rabbit CD4 (1:500, clone MAb KEN-4, Spring Val), rabbit CD8 (1:5000, clone MAb 12.C7, Spring Val), endothelial cell (CD31, 1:100, clone JC/70A, DAKO), rabbit macrophage (1:100, clone RAM 11, DAKO), and rabbit MHC II (1:100, clone Mab 45-3) were used.

Frozen sections were thawed and fixed with fresh acetone for 5 minutes. Endogenous peroxide activity was blocked with 0.3% hydrogen peroxide in phosphate buffered saline (PBS). After blocked with PBS and 1% bovine serum albumin (BSA), the specific primary antibodies were diluted in PBS with 1% BSA and incubated at room temperature for an hour. Detection was achieved using ABC Elite detection kit (DAKO) with aminoethylcarbizole as the chromogen. Sections were counterstained with light Mayers' hematoxylin, washed with tap water, and mounted in water soluble mounting medium (Biomeda, Catalogue no. MO1).

Control Group

Normal-dose PDT was performed as phase 1 in three rabbits.

Low-dose PDT Group

Immediately after each individual light treatment with normal-dose PDT, 5 mm Spot concentric with the 1.25 mm spot was exposed to 15 J/cm$^2$ (25 sec) in three rabbits. FA and fundus photography was taken as phase 1, and animals were sacrificed for immunohistochemical study at day 28 following PDT.

Results

Phase I
Photography

Fundus photography showed retinal whitening and localized elevation at day 1 and day 2, depigmented treatment area with patchy hyperpigmentation after day 7. FA showed early hypofluorescence in the treatment area due to nonperfusion and hyper flourescence at the border, and late pooling due to localized serous detachment and RPE disruption in day 1 and 2. At day 7, FA showed early and late central hypofluorescence probably due to non-perfusion. At day 14, 28, 42 and 56, FA findings are window defects due to depigmentation and blocked fluorescence due to hyperpigmentation. (Table 3). There was no neovascular leakages.

TABLE 3

Findings in fundus photography and fluorescein angiography

| Days after | Fundus photography | Fluorescein angiography |
| --- | --- | --- |
| 1 | Retinal whitening<br>Localized retinal elevation | Early hypofluorescence in the treatment area and hyperfluorescence at the border<br>Late pooling |
| 2 | Retinal whitening<br>Localized retinal elevation | Early hypofluorescence in the treatment area and hyperfluorescence at the border<br>Late pooling |
| 7 | Depigmented treatment area with hyperpigmentation | Central Hypofluorescence |
| 14 | Depigmented treatment area with hyperpigmentation | Blocked fluorescence and window defects |
| 21 | Depigmented treatment area with hyperpigmentation | Blocked fluorescence and window defects |
| 28 | Depigmented treatment area with hyperpigmentation | Blocked fluorescence and window defects |
| 42 | Depigmented treatment area with hyperpigmentation | Blocked fluorescence and window defects |
| 56 | Depigmented treatment area with hyperpigmentation | Blocked fluorescence and window defects |

Histologic Findings

RPE layer, photoreceptor layer, outer nuclear and plexiform layer were damaged in all cases. Inner nuclear layer shows a little damages but generally preserved well. Damage looks more severe with the higher dose of light especially in RPE layer showing more disarray in the higher dose. RPE layer began to become a monolayer again in two weeks. Choriocapapillariea were collapsed after PDT, but not the larger choroidal vessels.

Immunohistochemical Findings

CD4

CD4 positive cells were statistically significantly increased at day 2, day 7, day 14 and day 28 in all the dose of light except at day 14 with the light dose of 75 J/cm$^2$. In 6 weeks there were no significant increase in CD4 positive cells in treated area. A few CD4 positive cells were observed in the retina, but majority of the cells were in the choroid. (Table 4).

TABLE 4

The average number of CD4 positive cells in a 250 × 250 μm square segment of choroid after PDT

| Days after PDT | 75 J/cm$^2$ | 100 J/cm$^2$ | 150 J/cm$^2$ | Control |
| --- | --- | --- | --- | --- |
| 2 | 10.0 | | 8.3 | 2.0 |
| 7 | 10.0 | 9.8 | 10.8 | 3.0 |
| 14 | 2.5 | 6.7 | 7.7 | 2.7 |
| 28 | 4.3 | 12.5 | 9.7 | 2.3 |
| 42 | 0.5 | 0.5 | 2.5 | 0.5 |
| 56 | 0.8 | 0.7 | 1.0 | 0.8 |

CD8

CD8 positive cells were statistically significantly increased at all experimental days in all the dose of light. At day 2 there were no significant increase in CD8 positive cells. A few CD8 positive cells were observed in the retina, but majority of the cells wherein the choroid. (Table 5).

TABLE 5

The average number of CD8 positive cells in a 250 × 250 μm square segment of choroid after PDT

| Days after PDT | 75 J/cm$^2$ | 100 J/cm$^2$ | 150 J/cm$^2$ | Control |
| --- | --- | --- | --- | --- |
| 2 | 3.0 | | 1.0 | 0.5 |
| 7 | 5.5 | 4.0 | 4.5 | 0.5 |
| 14 | 3.5 | 4.8 | 7.0 | 0.8 |
| 28 | 5.0 | 5.0 | 7.5 | 1.0 |
| 42 | 6.0 | 5.0 | 3.5 | 0.5 |
| 56 | 4.4 | 2.9 | 3.8 | 1.5 |

Macrophage

Macrophages were statistically significantly increased at all experimental days in all the dose of light except at day 2 with the light dose of 75 J/cm². A few macrophages were observed in the retina, but majority of the cells were in the choroid. (Table 6).

TABLE 6

The average number of macrophages in a 250 × 250 μm square segment of choroid after PDT

| Days after PDT | 75 J/cm² | 100 J/cm² | 150 J/cm² | Control |
|---|---|---|---|---|
| 2 | 5.8 | | 15.1 | 5.0 |
| 7 | 8.0 | 12.3 | 13.3 | 5.0 |
| 14 | 8.0 | 6.5 | 7.0 | 4.5 |
| 28 | 8.0 | 13.0 | 10.2 | 3.6 |
| 42 | 7.7 | 7.0 | 7.3 | 4.3 |
| 56 | 14.0 | 11.8 | 12.4 | 2.8 |

MHC-II

MCH-II positive cells were statistically significantly increased at all experimental days in all the dose of light. (Table 7).

TABLE 7

The average number of MHC-II positive cells in a 250 × 250 μm square segment of choroid after PDT.

| Days after PDT | 75 J/cm² | 100 J/cm² | 150 J/cm² | Control |
|---|---|---|---|---|
| 2 | | | 17.5 | 1.5 |
| 7 | 10.5 | 14.5 | 15.3 | 6.5 |
| 14 | 16.8 | 23.0 | 24.3 | 5.3 |
| 28 | 12.0 | 24.0 | 19.3 | 6.0 |
| 42 | 16.0 | 18.0 | 22.7 | 6.3 |
| 56 | 9.0 | 11.1 | 13.6 | 3.7 |

CD31

At day 2 treated area shows CD31 positive cells in large choroidal vessels only. By day 7 treated area begins to show CD31 positive cells below the RPE layer probably representing choroidal vessels.

Phase 2. Dose Escalation

Photography

FA and fundus photographic features were similar to Phase 1.

Immunohistochemical Findings

At 4 weeks after low-dose PDT, CD4, CD8, Macrophage and MHC-II positive cells were slightly increased compare to control. (Table 8)

TABLE 8

The average number of positive cells in a 250 × 250 μm square segment of choroid after low-dose PDT.

| | 15 min. | 30 min. | 45 min. | Control |
|---|---|---|---|---|
| CD4 | 4.1 | 3.2 | 4.3 | 1.6 |
| CD8 | 2.3 | 1.1 | 1.4 | 0.7 |
| Macrophage | 5.4 | 5.5 | 6.5 | 3.5 |
| MHC-II | 7.7 | 8.1 | 8.4 | |

Phase 3

Photography

Fundus photography showed retinal whitening and localized elevation at day 1 and day 2, atrophic treatment area with surrounding hyperpigmentation after day 7. FA showed early hypofluorescence in the treatment area due to nonperfusion and hyper fluorescence at the border, and late pooling due to localized serious detachment and RPE disruption in day 1 and 2. At day 7, 14 and 28, FA showed window defects due to atrophy and surrounding window defects due to depigmentation and blocked fluorescence due to hyperpigmentation. There was no neovascular leakages.

Immunohistochemical Findings

At day 28, additional concentric large diameter low-dose PDT suppressed the increase in CD4, CD8, Macrophage and MHC-II positive cells after normal-dose PDT. Macrophage positive cells were slightly increased even after the additional low-dose PDT. (Table 9).

TABLE 9

The average number of positive cells in a 250 × 250 μm square segment of choroid after low-dose PDT

| | | 75 J/cm² | 100 J/cm² | 150 J/cm² | Control |
|---|---|---|---|---|---|
| CD4 | Therapeutic-dose | 3.0 | 4.9 | 5.0 | 1.6 |
| | Therapeutic-dose plus low-dose | 1.8 | 2.8 | 3.5 | 1.8 |
| CD8 | Therapeutic-dose | 4.4 | 3.5 | 3.3 | 0.7 |
| | Therapeutic-dose plus low-dose | 1.1 | 1.5 | 1.5 | 0.8 |
| Macrophage | Therapeutic-dose | 9.2 | 8.5 | 10.3 | 3.5 |
| | Therapeutic-dose plus low-dose | 5.1 | 6.6 | 5.4 | 3.5 |
| MHC-II | Therapeutic-dose | 9.6 | 10.7 | 11.3 | 3.7 |
| | Therapeutic-dose plus low-dose | 4.7 | 4.5 | 4.5 | 3.7 |

Conclusions

After therapeutic PDT of normal rabbit choroid, there were prolonged inflammatory reactions persisting for as long as 56 days. T-lymphocytes and macrophages were not only increased, but also activated, as evidenced by increased activity of MHC-II positive cells. These activated inflammatory cells might play a role in angiogenesis. Low dose light (15 J/cm²) effectively inhibited the increase in inflammation when administered following therapeutic PDT.

Without being bound by theory, low-dose PDT may inactivate inflammatory signaling directly induced in the area exposed to normal dose PDT. Alternatively, low-dose PDT may affect cells adjacent to, or in the neighborhood of, the area treated with normal dose PDT to produce an anti-inflammatory effect. As such, the entirety of the present invention may also be practice by providing low-dose PDT (as described herein) prior to, preferably immediately before, administration of normal dose PDT to prevent inflammation due to said normal (higher) dose PDT.

Example 2

Low Dose PDT as an Inhibitor of Inflammation

The inhibitory effects of low dose PDT on the inflammation induced by high dose PDT is evaluated in rabbits as follows. Animals are injected intravenously with 0.2 mg/kg Verteporfin for injection (VFI) and the retina is exposed to light at 600 mW/cm² as per the following schedule. In groups receiving both high and low doses of PDT, the low dose spot is concentric with the high dose spot. The spots are applied in the posterior pole such that the top of the larger of the two spots is approximately 1 long disc diameter from the bottom of the optic disc.

A VISULAS 690s laser capable of modifying the spot size during treatment is used to apply the light doses. Laser Light at 689 nm is delivered from a diode laser (VISULAS 690s, Carl Zeiss) using a slit lamp (SL-3E, Topcon) and a slit lamp delivery system (VISULINK PDT/U, Carl Zeiss). The treatments are performed using a Mainster Wide-Field PDT contact lens with a magnification factor of 0.68. The spot size is initially set using the slit lamp adapter and the slit lamp focusing bar and confirmed with a pair of precision calipers. The required light dose is calculated by the system and confirmed with a power meter (Lasercheck, Coherent Medical Laser).

The total laser power expected is calculated as follows:

$$\text{Total laser power (mW)} = 600 \text{ mW/cm}^2 \times (\pi d^2/4)$$

where d is the spot diameter in cm, determined by the Laserlink setting x contact lens magnification. (magnification=1/magnification factor).

The software for the diode laser (VISULAS 690s Software version 2.8AN, Carl Zeiss) is modified to allow the spot size to be changed during light application while maintaining a constant fluence rate; i.e. when the spot size is increased from 3.0 to 3.5 or 5.5 mm in diameter, the output power of the laser increases to maintain a constant fluence rate of 600 mW/cm$^2$. The normal and low dose exposures in groups 3 through 6 are applied continuously with the spot size changed during the treatment.

A total of 30 rabbits are used in this study. Rabbits are randomly assigned to the following 6 groups.

Group 1: Normal Dose Only Controls: Five (5) animals are exposed to 50 J/cm$^2$ on a 3.0 mm spot applied 15 minutes after injection of 0.2 mg/kg VFI.

Group 2: Low Dose Only Control: Five (5) animals are exposed to 6 J/cm$^2$ in a 5.5 mm spot applied 15 minutes after injection of 0.2 mg/kg VFI.

Group 3: Normal Dose plus Low Dose—3 J/cm$^2$, 3.5 mm diameter: Five (5) animals are injected intravenously with 0.2 mg/kg VFI. After 15 minutes, animals are exposed to high dose PDT of 50 J/cm$^2$ in a 3.0 mm spot and low dose PDT of 3 J/cm$^2$ applied concentrically in a 3.5 mm spot. This is accomplished by setting the laser to continuously deliver 50 J/cm$^2$ at a diameter of 3.0 mm while increasing the spot diameter quickly to 3.5 mm for the last 5 seconds of light treatment to deliver the remaining 3 J/cm$^2$. The result of this exposure will be a spot of 3.0 mm in diameter exposed to the high dose PDT (50 J/cm$^2$) surrounded by a ring of 3.5 mm in diameter exposed to a low dose PDT (3 J/cm$^2$).

Group 4: Normal Dose plus Low Dose—6 J/cm$^2$, 3.5 mm diameter Five (5) animals are injected intravenously with 0.2 mg/kg VFI. After 15 minutes, animals are exposed to high dose PDT of 50 J/cm$^2$ in a 3.0 mm spot and low dose PDT of 6 J/cm$^2$ applied concentrically in a 3.5 mm spot. This is accomplished by setting the laser to continuously deliver 50 J/cm$^2$ at a diameter of 3.0 mm while increasing the spot diameter quickly to 3.5 mm for the last 10 seconds of light treatment to deliver the remaining 6 J/cm$^2$. The result of this exposure is a spot of 3.0 mm in diameter exposed to the high dose PDT (50 J/cm$^2$) surrounded by a ring of 3.5 mm in diameter exposed to a low dose PDT (6 J/cm$^2$).

Group 5: Normal Dose plus Low Dose—3 J/cm$^2$, 5.5 mm diameter: Five (5) animals will be injected intravenously with 0.2 mg/kg VFI. After 15 minutes, animals are exposed to high dose PDT of 50 J/cm$^2$ in a 3.0 mm spot and low dose PDT of 3 J/cm$^2$ applied concentrically in a 5.5 mm spot. This is accomplished by setting the laser to continuously deliver 50 J/cm$^2$ at a diameter of 3.0 mm while increasing the spot diameter quickly to 5.5 mm for the last 5 seconds of light treatment to deliver the remaining 3 J/cm$^2$. The result of this exposure is a spot of 3.0 mm in diameter exposed to the high dose PDT (50 J/cm$^2$) surrounded by a ring of 5.5 mm in diameter exposed to a low dose PDT (3 J/cm$^2$).

Group 6: Normal Dose plus Low Dose—6 J/cm$^2$, 5.5 mm diameter: Five (5) animals are injected intravenously with 0.2 mg/kg VFI. After 15 minutes, animals are exposed to high dose PDT of 50 J/cm$^2$ in a 3.0 mm spot and low dose PDT of 6 J/cm$^2$ applied concentrically in a 5.5 mm spot. This is accomplished by setting the laser to continuously deliver 50 J/cm$^2$ at a diameter of 3.0 mm while increasing the spot diameter quickly to 5.5 mm for the last 10 seconds of light treatment to deliver the remaining 6 J/cm$^2$. The result of this exposure is a spot of 3.0 mm in diameter exposed to the high dose PDT (50 J/cm$^2$) surrounded by a ring of 5.5 mm in diameter exposed to a low dose PDT (6 J/cm$^2$).

When the light exposure is completed, the animals are returned to cage units in the housing area, and are kept in reduced lighting until the beginning of the next 12 hours of the dark/light cycle. The following morning, at the beginning of their 12 hour light cycle, light reducing drapes are removed from their cages.

Color fundus pictures are taken in non-anesthetized animals once daily for the first three days after PDT treatment and as required thereafter. Fluorescein angiography and fundus photographs is also performed on anesthetized animals 3 to 7 days before PDT treatment to gather baseline information and on Day 3 (and Day 7) after PDT as indicated by the length of the in-life phase (3 days or 7 days). Animals are euthanized after the time frame indicated in EX-01015. Eyes are collected for histology.

PDT treatment parameters for the combined normal and low dose PDT treatments may be summarized as normal dose (where it occurs) for 83 seconds followed by low dose for 5 or 10 seconds (as appropriate) to deliver 3 or 6 J/cm$^2$, respectively, and as indicated above. The above approach may also be conducted "in reverse" wherein the low dose PDT is provided first followed by normal dose PDT administered to the same or a smaller area. For example, the low dose PDT may first be administered in a circle which is then focused or restricted into a smaller concentric circle in which normal (higher) dose PDT is administered. The light doses of this embodiment may be as described above.

The above examples are included for illustrative purposes only and are not intended to limit the scope of the invention. Many variations to those described above are possible.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

The invention claimed is:

1. A method for reducing or treating inflammation arising from normal dose photodynamic therapy (PDT), which method comprises
   a) exposing a target tissue containing a photosensitizing agent in a subject to normal dose PDT treatment which results in inflammation in said target tissue; and
   b) exposing a tissue area that encompasses the target tissue to low dose light having a wavelength absorbed by the photosensitizing agent used in said normal dose PDT treatment for a time sufficient to reduce or treat inflammation arising from said normal dose PDT treatment;
   wherein step b) immediately follows step a);
   wherein the tissue area encompassing the target tissue in step b) is concentric with but larger than the target tissue in step a).

2. The method of claim 1 wherein said subject is human.

3. The method of claim 1, wherein the target tissue is an ocular tissue.

4. The method of claim 3, wherein the ocular tissue contains unwanted neovasculature.

5. The method of claim 4, wherein the unwanted neovasculature is choroidal neovasculature.

6. The method of claim 2, wherein the subject has been diagnosed or is afflicted with age-related macular degeneration (AMD).

7. The method of claim 2, wherein the subject has been diagnosed or is afflicted with a condition selected from macular degeneration, ocular histoplasmosis syndrome, pathologic myopia, diabetic macular edema, diabetic retinopathy, neovascular glaucoma, corneal neovascularization and inflammatory diseases.

8. The method of claim 1, wherein the photosensitizing agent is selected from a texaphyrin, a chlorin, a phthalocyanine, a purpurin, a bacteriochlorin, a porphyrin, a porphyrin derivative, a green porphyrin, a phthalocyanine and 5-aminolevulinic acid (ALA).

9. The method of claim 8, wherein the photosensitizing agent is a monohydrobenzoporphyrin compound.

10. The method of claim 9, wherein the photosensitizing agent is BPD-MA or verteporfin.

11. The method of claim 1, wherein the photosensitizing agent is applied topically to the subject.

12. The method of claim 1, wherein the photosensitizing agent is administered systemically to the subject.

13. The method of claim 1, wherein the low dose light is a dosage from about 1 J/cm$^2$ to about 10 J/cm$^2$.

14. The method of claim 1, wherein the dosage of the low dose light is about 15 J/cm$^2$.

15. The method of claim 1, wherein the low dose light irradiation lasts about 5 seconds.

16. The method of claim 1, wherein the wavelength of the low dose light is from about 350 nm to about 800 nm.

17. The method of claim 16, wherein the wavelength of the low dose light is about 689 nm.

18. The method of claim 1, wherein the inflammation is monitored by photography or immunohistochemistry.

19. The method of claim 18, wherein the photography is fundus photography.

20. The method of claim 19, wherein the tissue area is an ocular tissue and an inflammation marker is used to monitor the inflammation by fundus photography, wherein said inflammation marker is selected from retinal whitening, localized retinal elevation, depigmented treatment area with hyperpigmentation, early hypofluorescence in the treatment area, hyperfluorescence at the border, late pooling, central hypofluorescence and blocked fluorescence and window defects.

21. The method of claim 20, wherein the tissue area is an ocular tissue and an inflammation marker is used to monitor the inflammation by immunohistochemistry, wherein said inflammation marker is selected from CD4, CD8, CD31, macrophage and MHC II.

22. The method of claim 1, wherein the inflammation is monitored by scanning laser ophthalmoscopy (SLO) or optical coherence tomography (OTC).

23. The method of claim 1, further comprising a step of administering an immunosuppressive agent to the subject before the tissue area is exposed to low dose light.

24. The method of claim 1, further comprising a step of administering an antiangiogenic or a neuroprotective agent to the subject before the tissue area is exposed to low dose light.

25. The method of claim 1, wherein the photosensitizing agent is a BPD B-ring derivative.

26. The method of claim 25, wherein the BPD B-ring derivative is a hydrophilic or a lipophilic BPD B-ring analog.

27. A method of treating unwanted neovasculature of an eye, which method comprises:
   a) administering to a subject in need of treatment for unwanted neovasculature an amount of photosensitizer sufficient to permit an effective amount to localize in said neovasculature;
   b) permitting sufficient time to elapse to allow an effective amount of said photosensitizer to localize in said neovasculature;
   c) providing a first dosage of irradiation to a treatment area of the subject's eye containing said neovasculature with light having a wavelength that is absorbed by said photosensitizer for a sufficient time and at a sufficient intensity to occlude said neovasculature, wherein said first dosage of irradiation results in inflammation in said treatment area; and
   d) providing a second and lower dosage of irradiation to said treatment area and an additional area that encompasses said treatment area with light having a wavelength absorbed by the photosensitizer for sufficient time to reduce the effects of inflammation arising from said first dosage of irradiation;
   wherein step d) immediately follows step c); and
   wherein the area exposed to the lower dosage of irradiation in step d) is concentric with but larger than the treatment area exposed to the first dosage of irradiation in step c).

28. The method of claim 27, wherein the unwanted neovasculature is in the choroid of the subject's eye, and wherein the subject has been diagnosed or is afflicted with AMD, pathologic myopia, or ocular histoplasmosis.

29. The method of claim 1, wherein the target tissue in step a) is treated for neovasculature.

30. The method of claim 1 wherein the target tissue is exposed to a total dosage of irradiation of $\geq 50$ J/cm$^2$.

31. The method of claim 27 wherein the target tissue is exposed to a total dosage of irradiation of $\geq 50$ J/cm$^2$.

* * * * *